United States Patent
Philipp

Patent Number: 6,013,991
Date of Patent: Jan. 11, 2000

[54] MOTOR CONTROL CIRCUIT

[75] Inventor: Chris Philipp, Portage, Mich.

[73] Assignee: Stryker Corporation, Kalamazoo, Mich.

[21] Appl. No.: 08/990,605

[22] Filed: Dec. 15, 1997

Related U.S. Application Data

[63] Continuation of application No. 08/626,252, Mar. 29, 1996, Pat. No. 5,747,953.

[51] Int. Cl.$^7$ ....................................................... H02P 1/00
[52] U.S. Cl. ........................... 318/139; 318/114; 318/119; 318/280; 388/907; 388/937; 388/931
[58] Field of Search .................................... 318/139, 114, 318/119, 280; 388/907, 937, 931

[56] References Cited

U.S. PATENT DOCUMENTS

| | | | |
|---|---|---|---|
| 5,136,220 | 8/1992 | Philipp | 318/254 |
| 5,136,469 | 8/1992 | Carusillo et al. | 388/937 |
| 5,207,697 | 5/1993 | Carusillo et al. | 606/167 |
| 5,258,755 | 11/1993 | Kuckes | 388/937 |
| 5,426,355 | 6/1995 | Zweighaft . | |

*Primary Examiner*—Karen Masih
*Attorney, Agent, or Firm*—Flynn, Thiel, Boutell & Tanis, P.C.

[57] ABSTRACT

A motor controller for regulating the application of current to the windings of a motor in order to both control the actuation of the motor rotor and the braking of the rotor. The motor controller includes a speed control circuit regenerating a signal representative of the user-selected speed, a direction controller to signal if the motor is to be driven in the forward, reverse or oscillatory motion and a speed override circuit. There is also a current sensor for monitoring the current drawn by the motor, a brake controller and an energization circuit. The energization circuit regulates the application of a current to the motor to cause the rotation or braking of the rotor. When the motor is to be oscillated, each time the direction controller circuit transitions a FORWARD/REVERSE signal, the speed override circuit causes the energization circuit to momentarily apply energization signals to the motor based on the application of a zero-speed, user-speed signal. During such transitions, the current sensor sends a signal to the energization controller to make it appear that the motor is drawing in a large amount of current. Whenever the motor is operating at a speed higher than the user-speed, the brake controller causes the energization controller to apply braking current to the motor. However, if the rotor is not turning, the brake controller inhibits the assertion of the braking current.

29 Claims, 16 Drawing Sheets

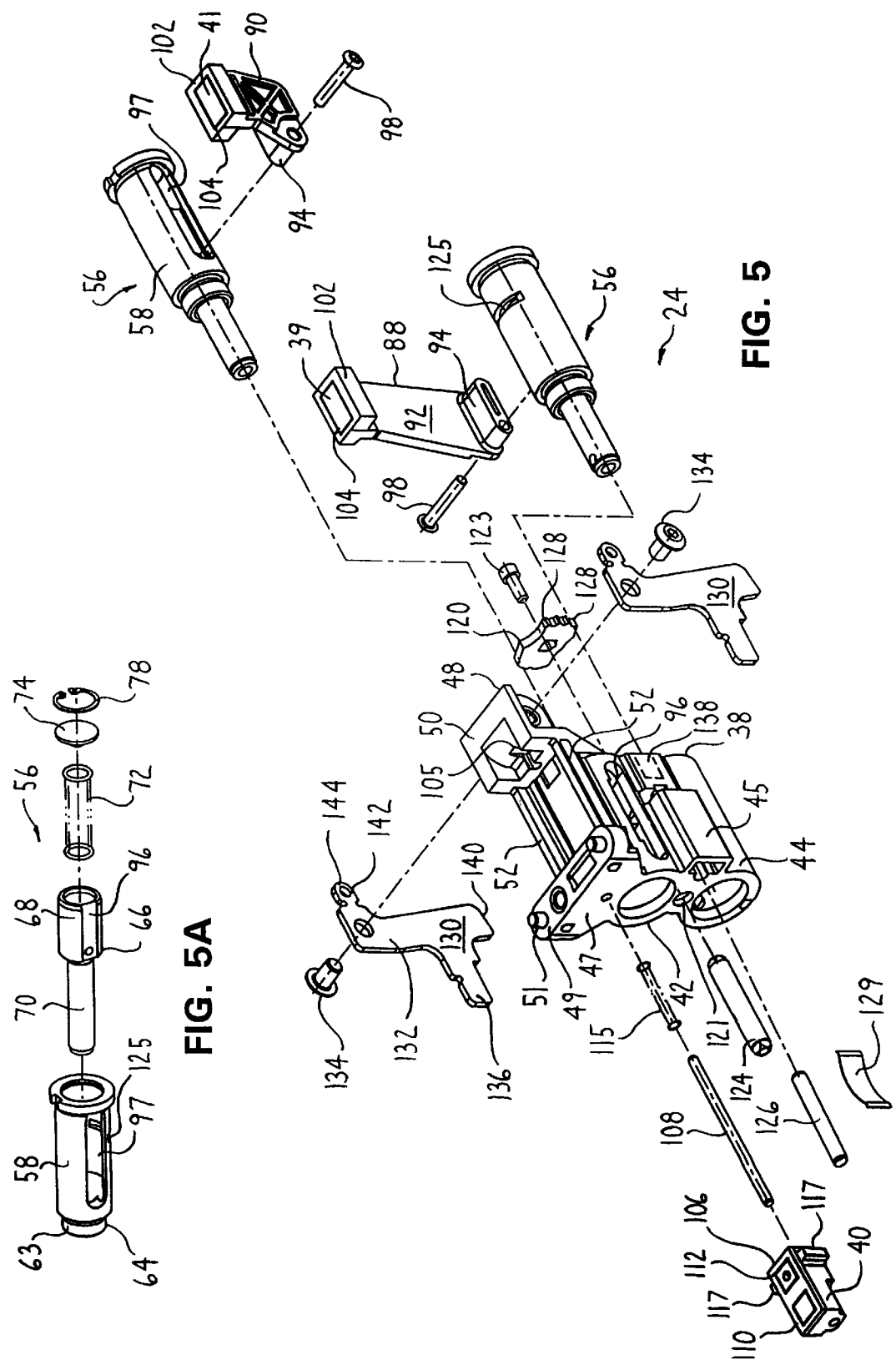

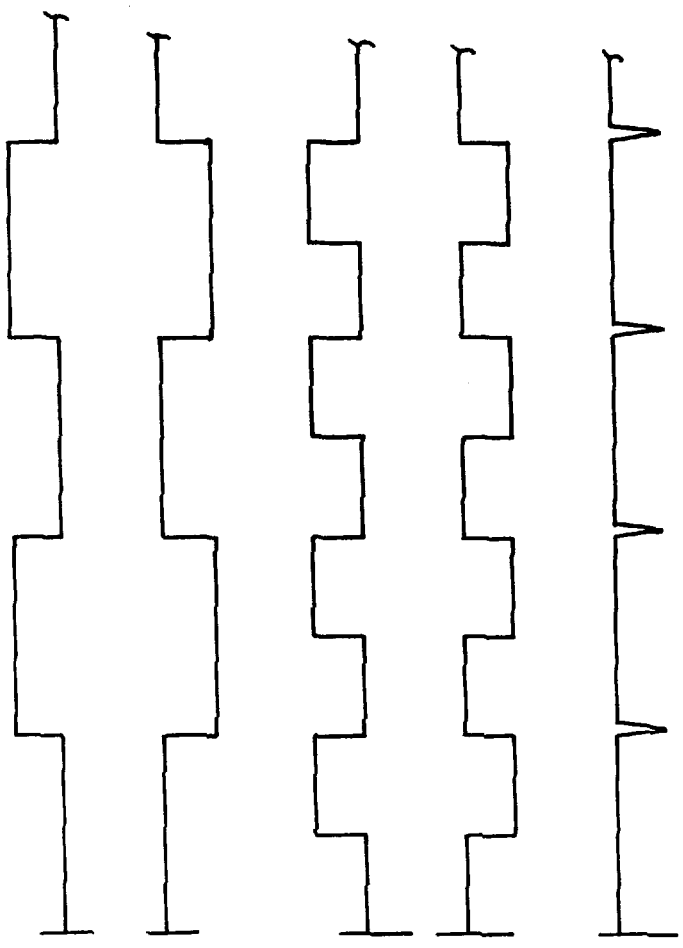

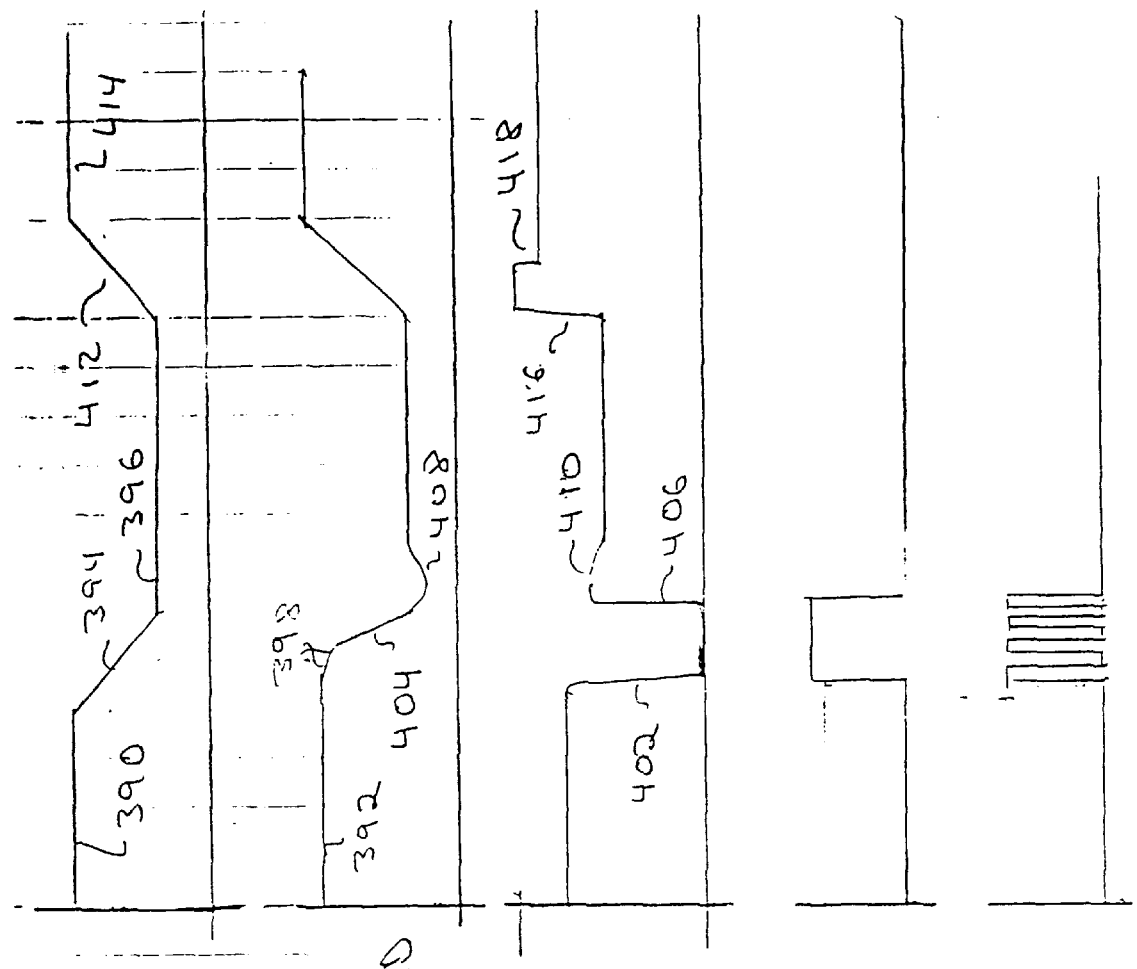

MOTOR CONTROL CIRCUIT

This is a continauation of Ser. No. 08/626 252, filed Mar. 29, 1996 now U.S. Pat. No. 5,747,953.

FIELD OF THE INVENTION

This invention relates generally to a motor control circuit.

BACKGROUND OF THE INVENTION

In modern surgery one of the most important instruments available to medical personnel is the powered surgical tool. Typically this tool comprises a drill unit in which a motor is housed. Secured to the drill unit is a cutting attachment that is designed to be applied to a surgical site on a patient in order to perform a specific medical procedure. For example, some powered surgical tools are provided with drills or burrs for cutting bores into hard tissue or for selectively removing hard tissue. Still other powered surgical tools are provided with saw heads. These tools are used for separating large sections of hard and soft tissue. The ability to use powered surgical tools on a patient has lessened the physical strain of physicians and other personnel when performing medical procedures on a patient. Moreover, most surgical procedures can be performed more quickly and more accurately with powered surgical tools than with the manual equivalents that proceeded them.

One type of powered surgical tool that is especially popular with some physicians is the cordless, battery operated powered surgical tool. As the name implies, this type of tool is provided with a battery that serves as the power source for the motor. This eliminates the need to provide the tool with a power cord that is connected to an external power source. Like many other powered surgical tools, a typical cordless, battery operated surgical tool has a handgrip similar to a pistol handgrip. The tool motor is contained within a housing located on top of and integral with the handgrip. The motor is typically actuated by an ON/OFF switch that extends forward from the front surface of the handgrip. The ON/OFF switch, in addition to controlling the ON/OFF state of the motor, also controls the energization current supplied to the motor so as to control the speed of the motor. The electronics that control the motor are typically located in the housing adjacent the motor. In a cordless surgical tool, the battery that supplies the energization current for the motor is typically housed in the handgrip.

The elimination of the power cord offers several benefits over corded, powered surgical tools. Surgical personnel using this type of tool do not have to concern themselves with either sterilizing a cord so that it can be brought into the sterile surgical field or ensuring that, during the medical procedure, an unsterilized cord is not inadvertently introduced into the surgical field. Moreover, the elimination of the cord results in the like elimination of the physical clutter and field-of-view blockage a cord otherwise brings to a surgical procedure.

While cordless surgical tools in many situations offer considerable improvements over their predecessors, they are not without some disadvantages. Many cordless powered surgical tools are provided with electro-mechanical ON/OFF switches. The ON/OFF switch, as well as the rest of the tool, is often placed in an extremely harsh environment in order to sterilize the tool. For example, it is not uncommon to sterilize a powered surgical tool by placing it in a chamber where the temperature is approximately 270° F., the humidity is at or near 100% and the atmospheric pressure is approximately 30 psi. The repeated exposure of the mechanical contact points of the ON/OFF switches employed in many surgical tools to this type environment causes the components of these switches to corrode. This corrosion, in turn, causes these switches to malfunction. As a result it has become necessary to replace the ON/OFF switches of some power tools at an expensively high frequency.

Moreover, when providing a powered surgical tool, it is desirable to design the tool so that the motor and associated cutting attachment can be rotated in first, forward direction and in a second, reverse direction. This minimal control over the direction of motor rotation makes it possible to drive a cutting attachment such as a drill in both forward and reverse directions so that the attachment can easily be forced into and removed from the surgical site.

It has also become increasingly desirable to design powered surgical tools, including cordless powered surgical tools, so that they oscillate the complementary cutting attachments between the forward and reverse rotations. It is, for example, desirable to drive a drill bit in an oscillatory rotational pattern when the bit is initially applied against bone; so driving the bit has been found to reduce the tendency of the bit to skew prior to the bore hole forming. It has also been found desirable to drive a drill bit in an oscillatory rotational pattern when it is used to cut through the opposed side of a bone. Driving a drill bit in this motion minimizes the extent to which soft tissue adjacent to the bone wraps around the bit as the bit exits the bone.

Problems have, however, arisen in providing some powered surgical tools, especially cordless powered surgical tools, with the ability to actuate the motors integral with these tools so that they undergo an oscillatory. rotation. In some tools, especially those like cordless tools wherein the motor is housed in a part of the tool separate from that handgrip held by the surgeon, the oscillatory motion has been found to vibrate the tool to such an extent that a surgeon cannot firmly hold it. This movement is sometimes referred to as tool "bucking". Moreover, a considerable amount of the power applied to these motors when they oscillate is apparently converted into heat instead of being used to actuate the associated cutting attachments. Over time, this heat, which is simply absorbed by the motors, can cause the motors themselves to wear out at a relatively high rate. A further undesirable side effect of this heating when it occurs in a cordless powered surgical tool is that it means energy from the battery that should be used solely to drive the cutting attachment is lost to needless tool heating.

Still another disadvantage of many powered surgical tools, including battery powered surgical tools, is that it has proved difficult to provide switches that allow the surgeon using the tool to easily control both the direction in which the tool motor turns (forward, reverse, or oscillatory) and the speed of the tool. Many powered surgical tools are designed so that the forefinger switch, (the trigger finger switch), located on the leading surface of the handgrip only controls the ON/OFF state of the motor and the motor speed. A second switch typically located along a rear surface of the tool is used to control motor rotation: forward; reverse; or oscillatory. A disadvantage of these tools is that each time the surgeon wants to change motor rotation, he/she must reposition his/her hand holding the tool to actuate the second switch or actuate this second switch with his/her other hand. Either procedure takes time and forces the surgeon to take his/her concentration away from the procedure being performed and, instead, apply it to the tool.

SUMMARY OF THE INVENTION

This invention relates to an improved cordless, battery operated powered surgical tool with contactless control switches that are conveniently placed to allow a surgeon to control both the direction and speed of tool motor rotation. Still another feature of the surgical tool of this invention is that it includes a motor control circuit that facilitates the oscillator motor rotation without inducing undesirable tool vibration.

BRIEF DESCRIPTION OF THE DRAWINGS

This invention is pointed out with particularity in the claims. The above and further features of this invention may be better understood by reference to the following description taken in conjunction with the accompanying drawings, in which:

FIG. 5 is an exploded view of the internal components of the trigger assembly;

FIG. 5A is an exploded view of the components within a shaft housing of the trigger assembly of FIG. 5;

FIGS. 10A, 10B, 10C, 10D and 10E are timing diagrams of signals generated by the motor control module to cause the oscillation of the drill unit motor; and FIGS. 11A, 11B, 11C, 11D and 11E are timing diagrams of the signals that cause the motor control module to assert the brake signals and of the brake signals themselves.

DETAILED DESCRIPTION

Figure 1:
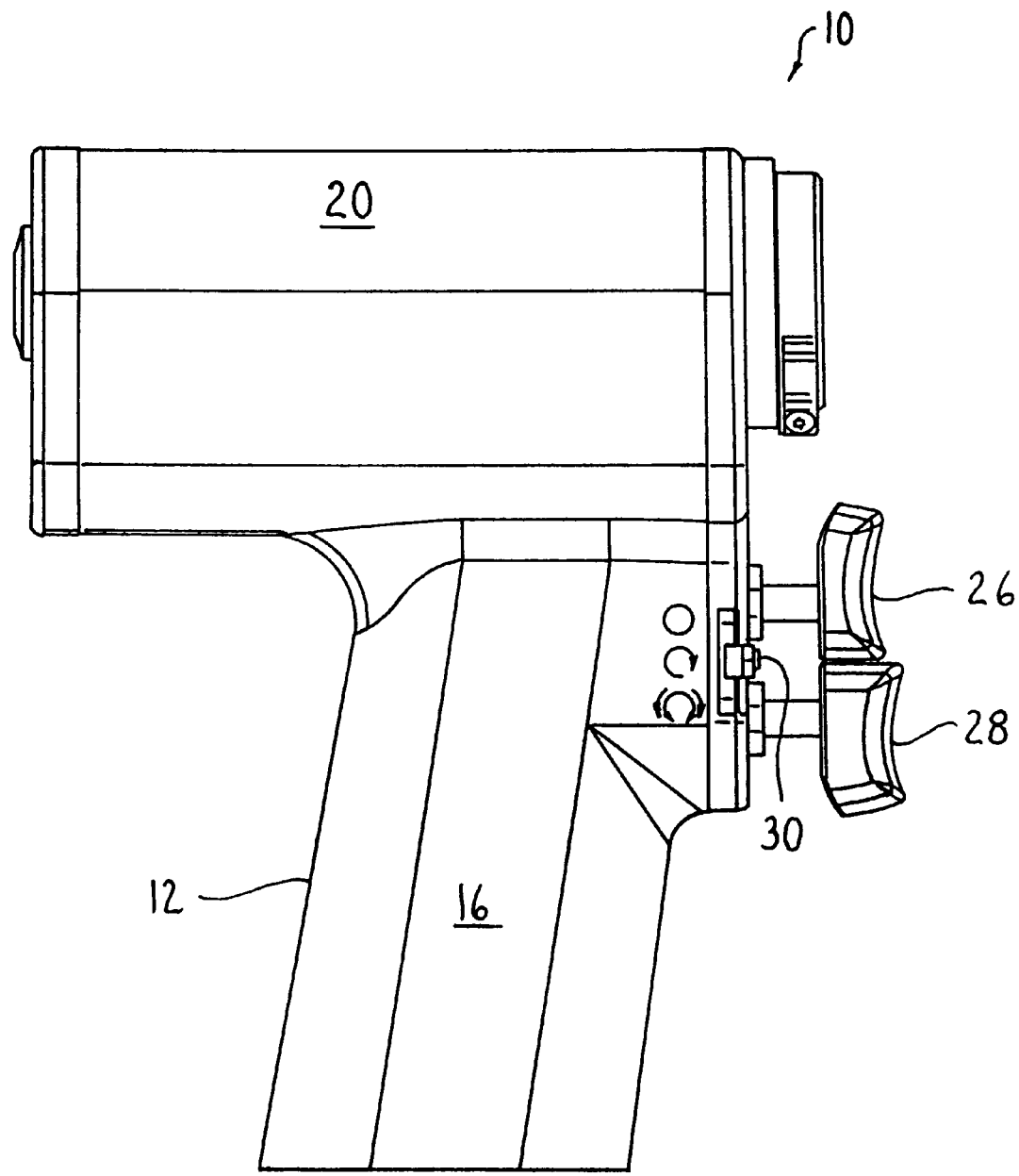
FIG. 1 is a side view of the drill unit that constitutes the cordless, battery operated power surgical tool of this invention which is conventionally known as a drill unit.
Figure 2:
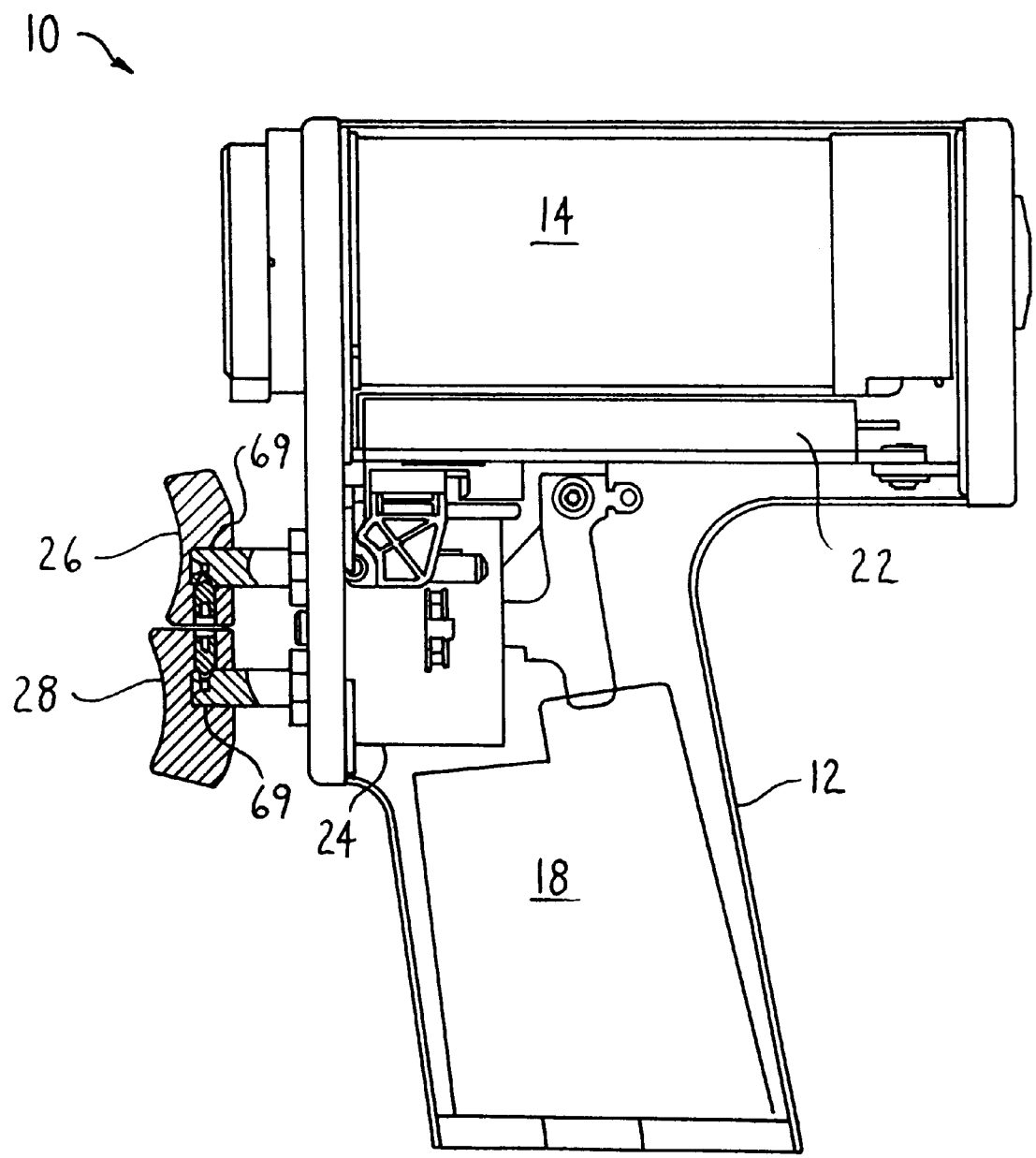
FIG. 2 is a side view showing the basic internal components of the drill unit.

FIGS. 1 and 2 illustrate the basic components of a cordless, battery operated powered surgical tool of this invention which is often referred to as a drill unit 10. Drill unit 10 includes a drill unit housing 12 which contains an electrically powered motor 14. The drill unit housing 12 has a lower section referred to as a handgrip 16. A battery 18 contained within the handgrip 16 supplies the power required to energize the motor 14. Formed integrally with the handgrip 16 and extending along the top of the handgrip is a motor section 20 in which the motor 14 is housed. Located immediately below the motor 14 is a sealed motor control module 22. The motor control module 22 regulates the application of energization signals to the motor 14 so as to cause the motor to selectively rotate in a first, forward direction, a second, reverse direction and in a third pattern wherein the motor undergoes an oscillatory rotation back-and-forth between the forward and reverse directions. (For many, but not all, powered surgical tools, when facing the front end of a tool, counter-clockwise rotation is considered to be forward rotation and clockwise rotation is considered to be reverse rotation.)

Located immediately below the motor control module 22 is a trigger assembly 24 that provides the switches that allow an individual to control the actuation of the motor 14 through the motor control module 22. Trigger assembly 24 has upper and lower vertically aligned trigger switches 26 and 28, respectively, that extend forward of the handgrip 16. By depressing upper trigger switch 26, medical personnel can cause the motor 14 to rotate in the reverse direction and control the speed of the motor's rotation. By depressing the lower trigger switch 23, medical personnel can cause the motor 14 to rotate in the forward direction and control the speed of the motor's rotation. By depressing both trigger switches 26 and 28, the motor 14 can be actuated into oscillatory rotation and the speed of the motor's rotation can also be controlled. The trigger assembly 24 also has a safety lever 30 that extends away from one side of the housing handgrip 16. Depending on the setting of the safety lever 30, the trigger assembly 24 inhibits movement of one or both of the trigger switches 26 and 28 so as to prevent unintended actuation of the motor 14.

Figure 3:
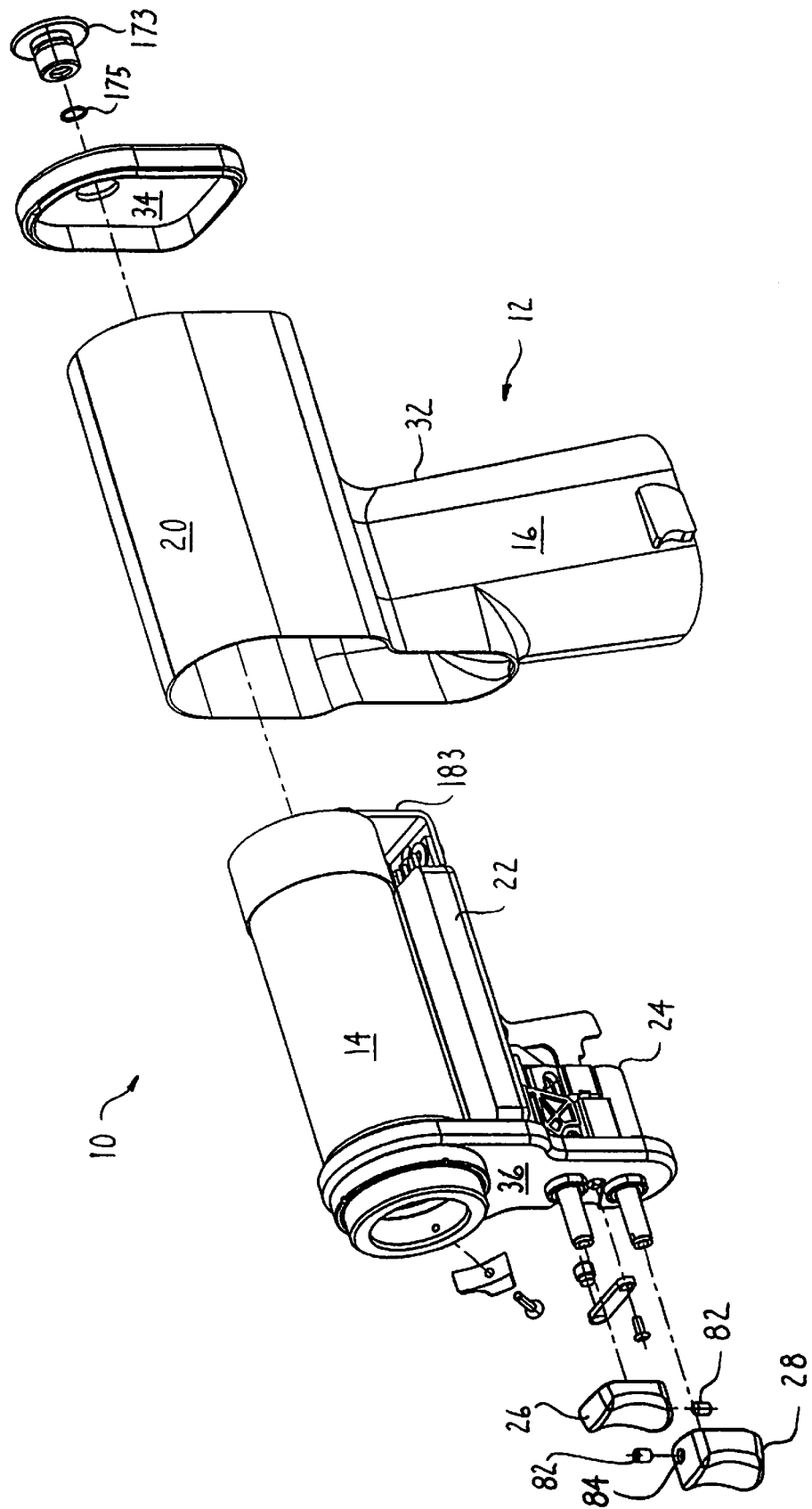
FIG. 3 is an exploded view of the external features of the drill unit.

The primary structural component of the drill unit housing 12, now described with respect to FIG. 3, is a weldment 32 which forms the sides of the handgrip 16 and housing motor section 20. The front and back ends of weldment 32 are open to facilitate the installation of the motor 14, the motor control module 22 and the trigger assembly 24 into the drill unit housing 12. A backcap 34 is fitted over the open rear end of the weldment 32. A front plate 36 is secured over the open front end of the weldment 32. In the illustrated version of this invention, the motor 14, the motor control module 22 and the trigger assembly 24 are all attached to the front plate 36. This subassembly is then fitted into the drill unit housing 12 as part of the process of assembling the drill unit 10 of this invention.

Figure 4:
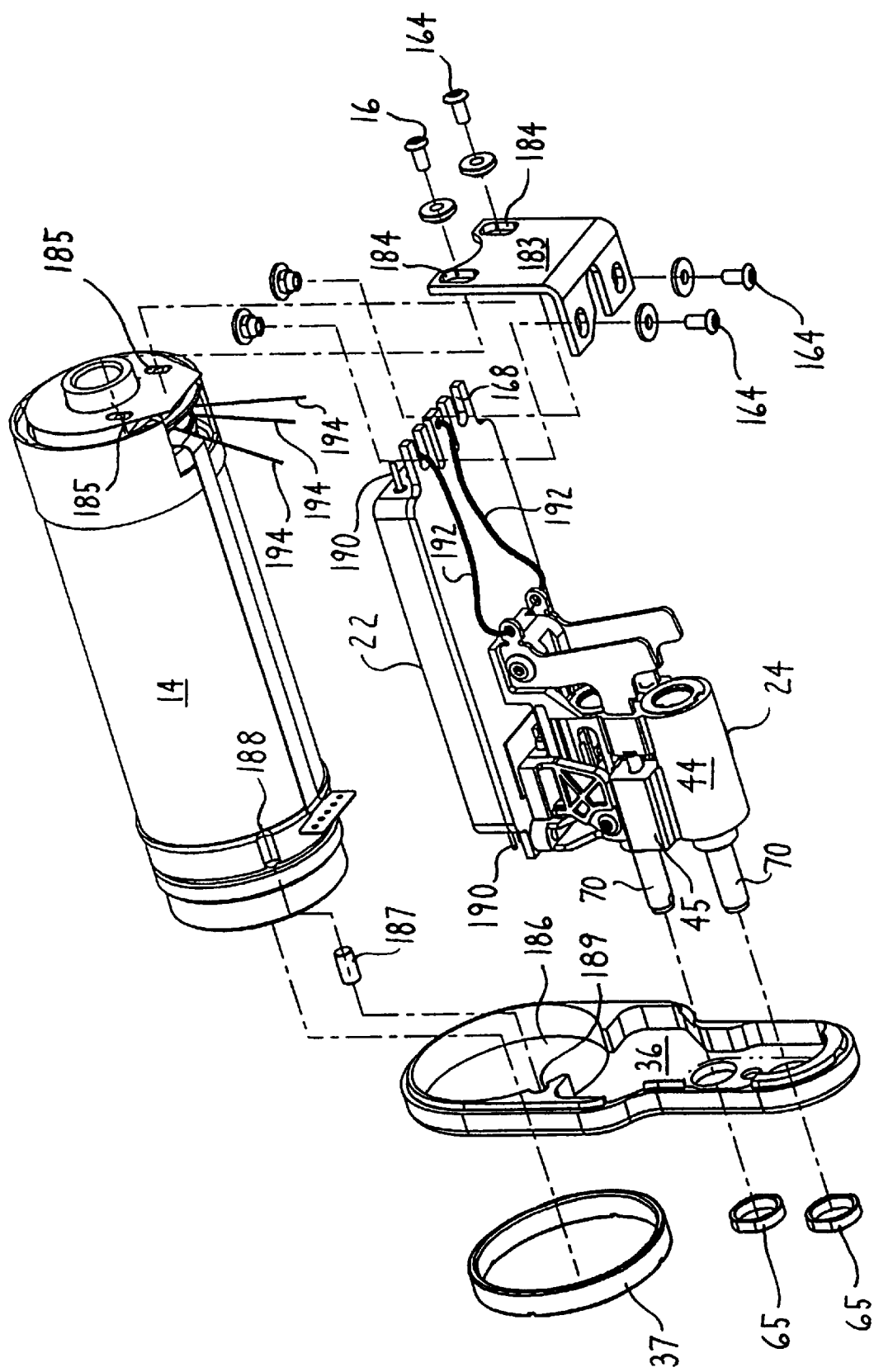
FIG. 4 is an exploded view illustrating how the motor, the motor controller, the trigger assembly and the housing front plate are assembled together.

The trigger assembly 24, as depicted in FIGS. 4 and 5, includes a single-piece trigger housing 38 that is located against the inside surface of the front plate 36 adjacent the lower end of the front plate. Three magnets 39, 40 and 41 are slidably secured to the top of the trigger housing 38 so as to move in response to the actuation of the trigger switches 26 and 28. Sensors 178–182 (FIG. 7B) internal to the motor control module 22 and located above the magnets 39, 40 and 41, monitor the positions of the magnets so as to cause the components internal to the module to apply the appropriate energization signals to the motor 14.

The trigger housing 38 includes upper and lower shaft sleeves 42 and 44, respectively, that are vertically aligned with each other. Upper shaft sleeve 42 houses the components associated with upper trigger switch 26. Lower shaft sleeve 44 houses the components associated with lower trigger switch 28. An elongated safety sleeve 45 is located on one side of the trigger housing 38 between the shaft sleeves 42 and 44 and extends from the forward end of the housing to approximately the midpoint of the housing. The safety 45 houses some of the components associated with sleeve safety lever 30.

A head member 47 extends upwardly above the forward end of the upper shaft sleeve 42. A tail member 48 is also integrally attached to the upper shaft sleeve 42 so as to be positioned above and behind the sleeve 42. Trigger housing head member 47 is formed with a top surface 49. Trigger housing tail member 48 is formed with a top surface 50 that is coplanar with the top surface 49 of trigger housing head member 47. The head member and tail member too surfaces 49 and 50, respectively, serve as the surfaces of the trigger assembly 24 on which the motor control module 22 is seated. Trigger housing head member 47 is further provided with spaced apart guide pins 51 that extend upwardly from the head member top surface 49. As will be described hereinafter, the guide pins 51 facilitate the proper seating of the motor control module 22 on the trigger assembly 24.

Trigger housing 38 is further formed with a pair of parallel rails 52 that extend across the top of the trigger housing upper sleeve 42 between the trigger housing head and tail members 47 and 48, respectively. The opposed left and right magnets, magnets 39 and 41, respectively, are each located above separate ones of the rails 52. The center magnet, magnet 40, is located above and between the rails 52, between the right magnet 39 and the left magnet 41.

Figure 5B:
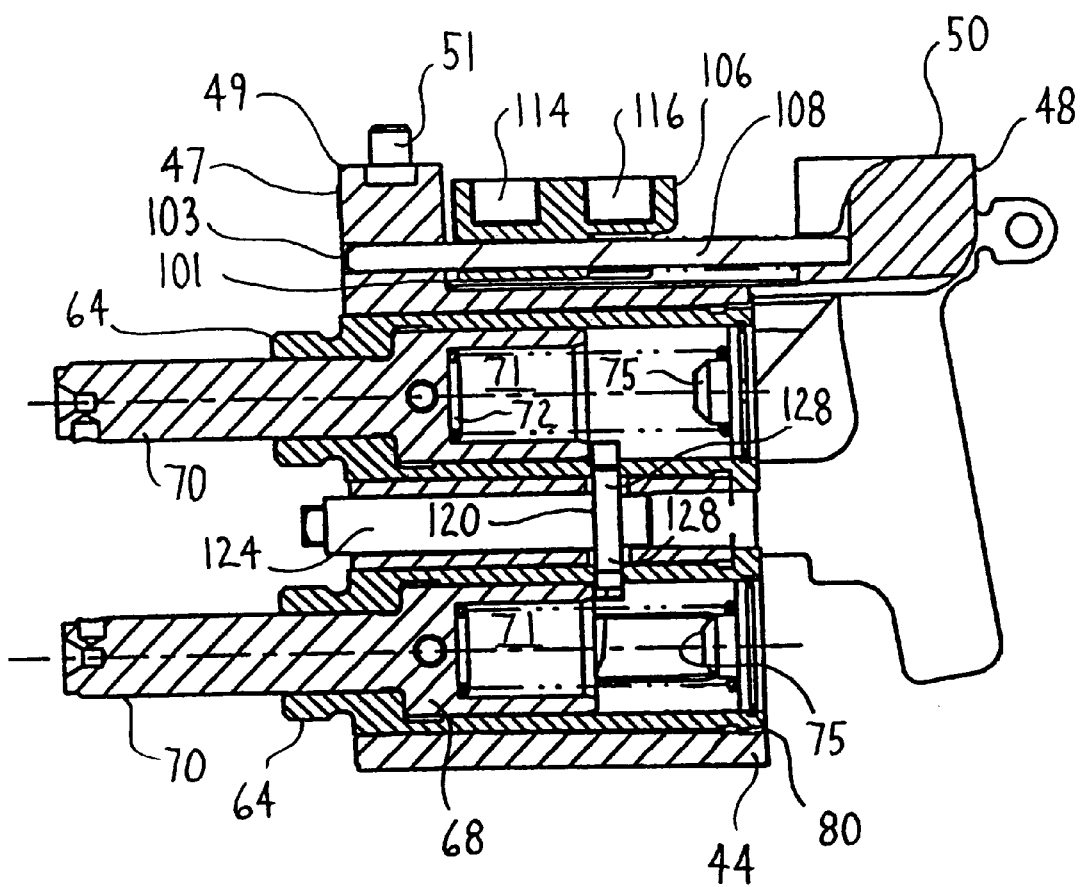
FIG. 5B is a cross sectional view of the trigger assembly of FIG. 5.

Housed inside each shaft sleeve 42 and 44 is a trigger shaft assembly 56 one of which is now described by reference to FIGS. 5A and 5B. The trigger shaft assembly 56 includes a metal-formed shaft housing 58. The shaft housing 58 is formed with a head end 64 that has a diameter less than that of the main body of the housing 58. The head ends 64 of the shaft housings 58 are formed with external threading 63. These head ends 64 of the shaft housings 58 extend through the adjacent front plate 36. Complementary nuts 65 (FIG. 4) are secured over the head ends 64 of the shaft housings 58 that project outside of the front plate 36 so as to fasten the shaft housings 58, as well as the whole of the trigger assembly 24, to the front plate 36.

A trigger shaft 66 is positioned in the shaft housing 58 so as to extend out of the head end 64 of the housing 58. The trigger shaft 66 is shaped to have a large diameter, generally cylindrically shaped base 68 that is disposed entirely within the shaft housing 58. Trigger shaft base 68 is further dimensioned to be able to slide in the shaft housing 58 and has a length approximately one-half of the length of the space in which it can slide. A shaft stem 70 that is coaxial with the trigger shaft base 68 extends forward from the base out of the shaft housing 58 and through the front plate 36. A spring 72 seated in the shaft housing 58 behind the trigger shaft base 68 biases the trigger shaft 66 so that the trigger shaft stem 70 normally extends out of the shaft housing 58. In the illustrated version of the invention, the base 68 of the trigger shaft 66 is formed with an axially aligned, rearward opening bore 71 in which the leading end of the spring 72 is seated. A generally disk shaped spring retainer 74 is located in the rear end of the shaft housing 72 so as to provide a rear stop for the spring 72. Spring retainer 74 is formed with a center boss 75 around which the spring 72 is seated. The spring retainer is held in position by a C-shaped retaining ring 78 that is seated in a groove 80 formed in the inside wall of the shaft housing 58.

Returning to FIGS. 2 and 3, it can be seen that the trigger switches 26 and 28 are attached to the ends of the trigger shaft stems 70 that extend forward of the front plate 36. Each switch 26 and 28 is formed with a bore, 69 in which the end of the complementary trigger shaft stem 70 is seated. A set screw 82 seated in a complementary threaded screw bore 84 formed in each switch 26 and 28 is positioned to abut against the side of the trigger shaft stem 70 seated in the trigger switch 26 or 28 in order to secure the switch to the trigger shaft stem 70.

The left and right magnets 39 and 41, respectively, are mounted in left and right magnet carriers 88 and 90, respectively, that move in unison with the displacement of the trigger shafts 66 as is best shown in FIG. 5. The magnet carriers 88 and 90 are located on the opposed sides of the trigger housing 38. Each magnet carrier 88 and 90 is formed out of a single piece of material that is shaped, in part to form a side plate 92. The side plate 92 integral with the left magnet carrier 88 extends from the axis of the trigger housing lower shaft sleeve 44 to the rail 52 on the right side of the trigger housing 38. The side plate 92 integral with right magnet carrier 90 extends from the axis of the trigger housing upper shaft sleeve 42 to the top of the rail 52 on the left side of the trigger housing 38. A foot 94 is attached to the bottom edge of each side plate 92 and extends perpendicularly inward from the side plate. Each foot 94 is secured to the trigger shaft 66 with which the magnet carrier 88 or 90 is associated. Each foot 94 extends through an elongated slot 96 formed in the associated shaft sleeve 42 or 44 and a similar slot 97 formed in the adjacent trigger shaft housing 58. Each foot 94 is seated in a rectangular profile groove 96 formed in the outer surface of the base 68 of the trigger shaft 66 with which the magnet carrier 88 or 90 is associated. A pin 98 that extends through the magnet carrier foot 94 and into the trigger shaft 66 ensures that the magnet carrier 88 or 90 moves in unison with the displacement of the trigger shaft.

A head piece 102 is attached to the top of each magnet carrier 88 and 90. Each head piece 102 is generally rectangularly shaped and is positioned to extend over the rail 52 adjacent to the magnet carrier 88 or 90. The top of the head piece 102 is shaped to define a rectangular recess 104 in which the associated left magnet 39 or right magnet 41 is seated. When one of the trigger switches 26 or 28 is depressed, the resultant motion of the associated trigger shaft 66 and magnet carrier 90 or 88 causes either the right or left magnet 41 or 39 to be moved longitudinally across the top of the trigger housing 38.

The center magnet 40, now described with reference to FIGS. 5 and 5B, rides in a center carrier 106 located between the head pieces 102 in which the left and right magnets 39 and 41, respectively, are carried. The center carrier 106 is a block-like structure that has a center rib 101 that extends downwardly from the main body of the carrier and that extend along the longitudinal axis of the carrier. The center carrier 106 is further dimensioned to extend rearward of the adjacent magnet carrier head pieces 102 when all of the carriers 88, 90 and 106 are located adjacent the trigger housing head member 47.

The center carrier 106 slides over a straight pin 108 that extends between the head member 47 and tail member 48 of the trigger housing 38. More specifically, one end of straight pin 108 is compression fitted in a bore 103 formed in the head member 47. The opposed end of the pin 108 is compression fitted in a rectangular cut-out 105 formed in the tail member 48. The straight pin 108 is further slidably fitted into a pin bore 109 that extends axially through the carrier center rib 101. The center rib 101 of the center carrier 106 is dimensioned to extend down to the top surface of the adjacent upper sleeve 42 in order to ensure lateral stability of the center carrier 106 as it is displaced.

The top surface of the center carrier 106 is formed with two, longitudinally aligned rectangular recesses 110 and 112. Two magnets 114 and 116 are respectively disposed in the individual recesses 110 and 112. Magnets 110 and 112 collectively comprise the center magnet 40. Magnets 114 and 116 are arranged in center carrier 106 so that one magnet has a north pole that faces the adjacent motor control module 22 and the second magnet has a south pole that faces the motor control module.

The center carrier 106 and associated magnets 114 and 116 are normally biased toward the trigger housing head member 47 by a spring 115 fitted over straight pin 108. The spring 115 extends between the trigger housing tail member 48 and the back end of the center carrier 106. The center carrier 106 is further provided with tabs 117 that project outwardly from the opposed sides of the carrier 106. Each tab 117 is positioned to abut the end surface of the adjacent magnet carrier head piece 102. Consequently, when the actuation of a trigger switch 26 and/or 28 results in the like displacement of the right or left magnet carrier 90 or 88, the rearward movement of the carrier 90 or 88 causes the like rearward movement of center carrier 106.

The trigger assembly 24 is further provided with a safety disk 120 positioned to selectively prevent unintentional actuation of the trigger switches 26 and 28. The safety disk 120 is housed in a slot 122 defined in the trigger housing in the portion of the housing between the shaft sleeves 42 and 44. More specifically, the safety disk 120 is positioned to be at a location where, when the trigger shafts 66 are in their full forward positions, the disk 120 can abut the rear ends of the trigger shafts 66. The safety disk 120 is secured to a cylindrical safety shaft 124 by a screw 123. Safety shaft 124 is rotatably fitted in a shaft bore 121 that extends axially through the portion of the trigger housing 38 between the shaft sleeves 42 and 44. The safety lever 30 (FIG. 1) is attached to the front end of the safety shaft 124 for rotating the shaft 124 and the safety disk 120. Each trigger shaft housing 58 is formed with a slot 125 dimensioned to accommodate the safety disk 120.

The safety disk 120 can be rotated into one of three positions. The disk 120 has a first position wherein it is spaced away from the spaces in both the upper and lower shaft sleeves 42 and 44 in which the associated trigger shafts 68 may slide. The safety disk 120 has a second position wherein the disk is disposed in the upper shaft sleeve 42 to prevent movement of the reverse trigger shaft 68. When in the third position, the safety disk 120 is disposed in both shaft sleeves 42 and 44 to prevent movement of both trigger shafts 68. The safety disk is held in an appropriate position by a cylindrical lock pin 126. Lock pin 126 is seated in a circular groove formed in the trigger housing safety sleeve 45. The lock pin 126 is positioned to be seated in one of a number of circular notches 128 formed along the adjacent side of the safety disk 120. A curved leaf spring 129 disposed in the safety sleeve 45 bears against the lock pin 126 to hold the pin 126 in the notch 128 in which the pin is seated. The force imposed by spring 129 to hold the safety disk 120 in position can be overcome by the manual displacement of safety lever 30.

A pair of conductive battery blades 130 are secured to the end of the trigger assembly 24. The battery blades 130 form part of the conductive paths between the battery 18 and the motor control module 22. Each battery blade is formed out of a single piece of conductive metal that is shaped to have an elongated, generally vertically aligned shank 132. The individual battery blades 130 are suspended to opposed sides of the trigger housing tail member 48 by button head screws 134 that extend through the shanks 132 forming each blade 130. Each battery blade 130 is further formed with a mounting tab 136 that extends perpendicularly forward of the associated shank 132 at a location approximately one-quarter the distance from the bottom edge surface of the shank. Each mounting tab 132 is compression fitted in a slot 138, (one slot shown in phantom,) formed on the side trigger housing 38.

The bottom end of shank 132 of each battery blade 130 functions as a male terminal 140 that is seated in a complementary conductive female terminal integral with the battery 18, (female terminal not shown). A conductor tab 142 extends rearward from each shank 142 adjacent the point the shank is secured to the trigger housing tail member 48. Conductor tab 142 is formed with an opening 144 to facilitate the securing of an insulated power conductor 146 to the battery blade 130.

Figure 6:
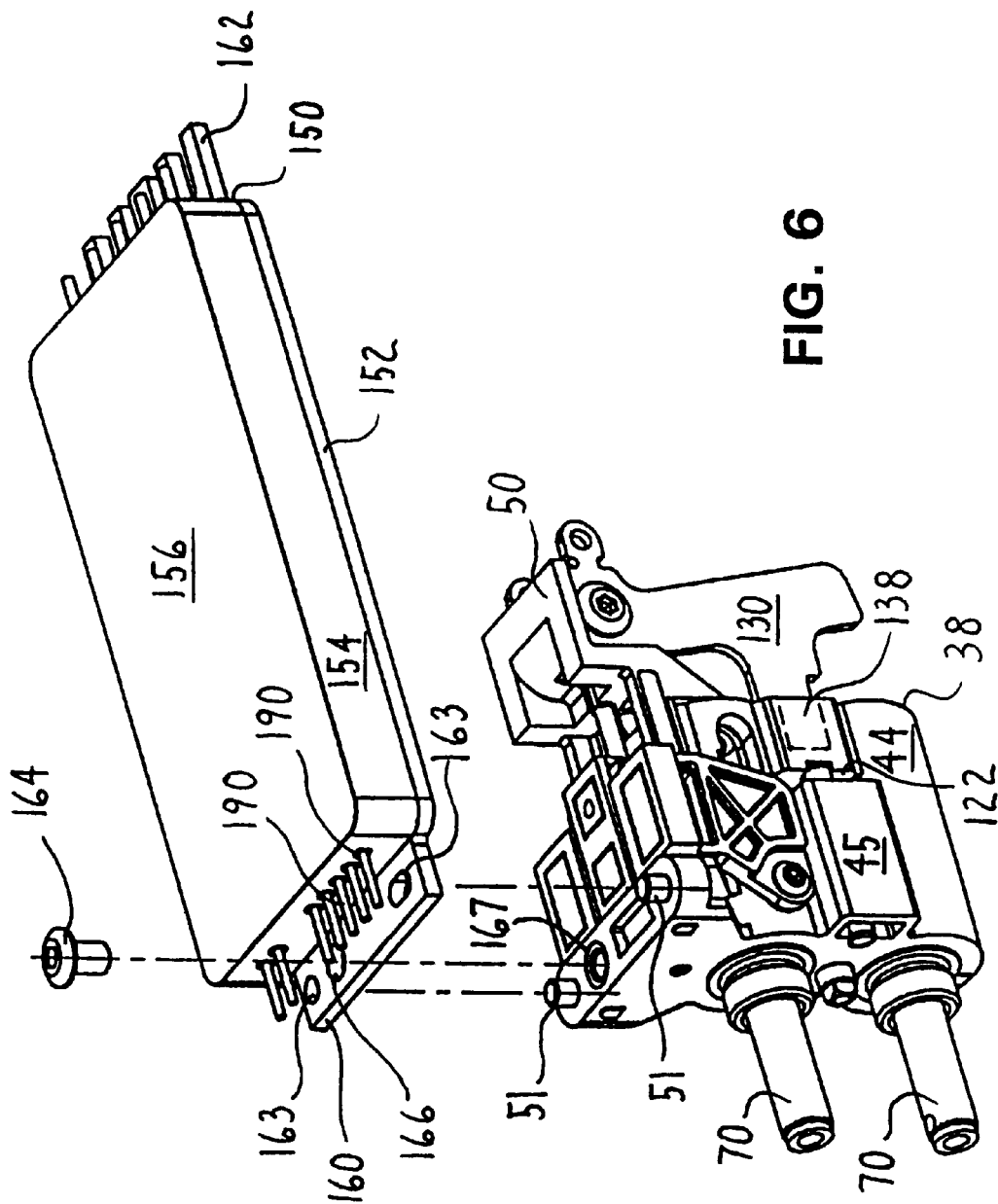
FIG. 6 is a an exploded view illustrating how the motor control module is secured to the trigger assembly in order to form the contactless switches of this invention.

The motor control module 22 is now initially described with reference to FIGS. 4 and 6. The motor control module 22 includes a module housing 150 that is secured to the top of the trigger assembly 22. The module housing 150 is formed out of a base plate 152, a generally rectangularly shaped corral 154 that forms the sides of the housing and a cover 156. The plate 152, the corral 154 and the cover 156 forming the module housing are bonded together to form an interior space, not identified, that is sealed from the outside environment. The components forming the control circuit of the drill unit 10 of this invention are housed in the interior space of the module housing 150. In preferred versions of this invention, bottom plate 152, corral 154 and cover 156 are formed of plated, rust-resistant cold-rolled steel.

Module housing base plate 152 is formed with forward and rearwardly extending tabs 160 and 162, respectively, that extend beyond the adjacent surfaces of the housing corral 154. Forward tab 160 is formed with two spaced apart guide holes 163. When the motor control module 22 is placed over the trigger assembly, the guide pins 51 associated with the trigger housing head member 47 are seated in the base plate guide holes 163 to ensure proper position of the motor control module. The motor control module 22 is secured to the trigger assembly 24 by a button-head screw 164 that is fitted into complementary, coaxial openings 166 and 167 formed respectively in the base plate forward extending tab 160 and in the trigger housing head member 47.

The base plate rearward extending tab 162 is formed to define a number of parallel cut-out slots 168 that are positioned along the length of the tab. These slots 168 facilitated the securement of fastening members to the module housing base plate 152 that are used to secure the motor control module 22 to the motor 14.

Figure 7B:
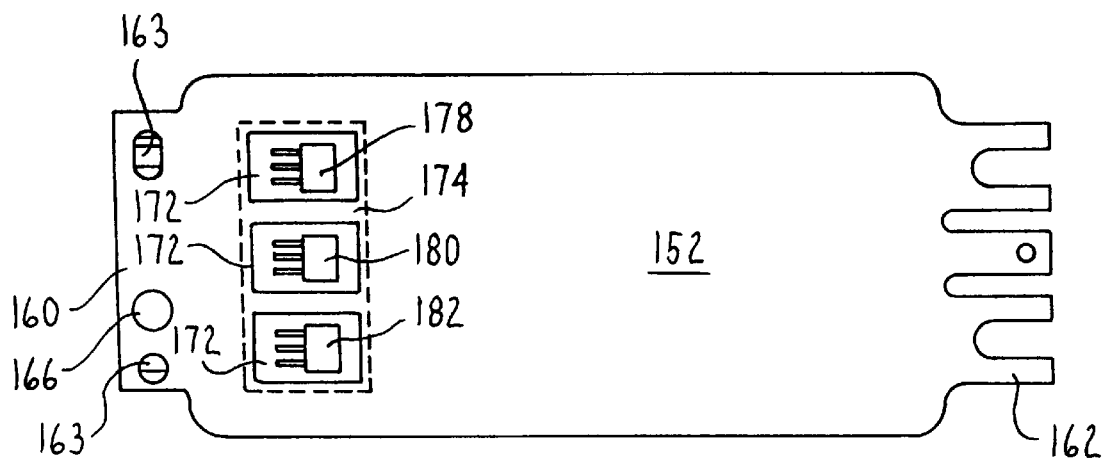
FIGS. 7A and 7B are respectively, cross sectional and bottom views of the bottom plate of the motor control module housing and of the magnetic-field sensors seated in the bottom plate.
Figure 7A:
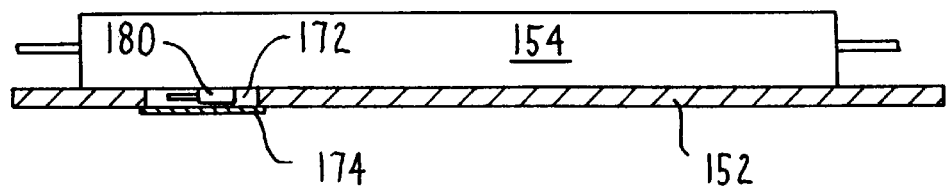

While the module housing 150 is primarily formed out of solid steel structural members, the housing base plate 152 is provided with three rectangular cutouts 172 now described by reference to Figures 7A and 7B. Each cutout 172 is formed in the housing base plate 152 so as to be axially aligned with and centered over the linear travel path of a separate one of the three trigger assembly magnets 39, 40 or 41. Collectively, the cutouts 172 are sealed by a single piece of thin metal seal 174 that is secured to the outer surface of the housing base plate 152. The metal forming the seal 174 is more magnetically permeable than the metal forming the module housing 150 to which the seal is attached. In one preferred version of the invention seal 174 is formed of a strip of molybdenum that is between 10 and 50 mils thick and, in more preferred versions of the invention, approximately 15 mils (0.015 inches) thick.

In the interior space within the module housing 150, and seated inside each base plate cutout 172 are individual Hall effect sensors 178, 180, and 182. These sensors 178, 180 and 182 are components integral with the motor control module 22 that regulate the energization of the motor 14. Since each Hall effect sensor 178, 180 and 182 is seated in a cutout adjacent a separate one of the trigger assembly magnets 39, 40, and 41, each sensor is paired with a separate one of the magnets. When an appropriate signal is applied across each Hall effect sensor 178, 180 or 182, a signal representative of the magnetic field in the vicinity of the sensor is generated by the sensor. In one preferred version of this invention, sensors 178 and 182 are magnetically unipolar and sensor 180 is magnetically bipolar. Thus, each Hall effect sensor 178, 180, and 182 generates a signal representative of the position of the of complementary moving trigger assembly magnet 39, 40 or 41, respectively, relative to the sensor. As will be described hereinafter, the signals produced by the Hall effect sensors 178, 180 and 182 are then, in turn, used by other components of the motor control module 22 as input signals for regulating the application of energization signals to the motor 14.

Returning to FIGS. 3 and 4, it can be seen that the rear end of the motor 14 secured to the backcap 34 by a decorative screw 173. An O-ring 175 s seated in a groove 175 formed in shaft of the screw 173 in order to hold the screw in position. The front end of the motor 14 extends through a larger, circular opening 186 formed in the front plate 36. The motor 14 is held in position by a ring nut 37. A cylindrical lock pin 187 is disposed between the motor 14 and the front plate 36. The lock pin 187 is seated in complementary semi-circular notches 188 and 189 formed, respectively, in the side of the motor and the surface of the front plate 36 that defines opening 186.

Not illustrated and not part of this invention is a collet, a chuck or a saw attachment that may be secured to the exposed end of the motor rotor 203 (FIG. 8) that extends through the front plate 36. The collet, the chuck or the saw attachment functions as the element of the drill unit 10 to which the complementary cutting attachment with which the drill unit is used is attached. It should also be recognized that while element 14 is generally representative of the motor of the drill unit 10 of this invention that integral with the motor is a gear assembly for transferring the rotational moment generated by the motor rotor 203 to the collet, the chuck or the saw attachment.

An L-shaped bracket 183 extends downwardly and then forward from the rear end of the motor 14. A first set of button head screws 164 secure the bracket 183 to the rear end of the motor 14. These screws 164 extend through complementary slots 184 formed in the bracket 183 and are secured in complementary bores 185 formed in the rear end of the motor 14. A second set of screws 164 secure the rearward extending tab 162 of the motor control module housing 150 to the bracket 164 so as to hold the rear of the housing in position. These pins 164 are seated in the complementary slots 168 formed in the tab 162.

A number of conductive pins 190 that extend out of the opposed front and rear ends of the module housing 150. Conductive pins 190 serve as part of the conductive paths for the signals applied to the motor 14 and the signal received from the motor 14 that are employed to monitor the state of the motor. Each conductive pin 190 extends out through an opening in the housing corral 154; a glass or other non-conductive material is used to form an environmental seal around the pins, (corral openings and glass seal not shown). A first shielded wire 192 extends from one of the battery blades 130 to the rearward extending tab 162 integral with the housing base plate 152. A second shielded wire 192 extends from the other battery blade 192 to one of the rearwardly extending conductive pins 190. Additional wires 194 that extend from the rear of the motor 14 to other of the rearwardly extending conductive pins 190 serve as the conductive paths to the windings forming the motor 14.

The relationship between the motor 14 and the circuitry forming the motor controller module 22 is now initially discussed with reference to the block diagram of FIG. 8. The motor 14 is a three phase, full-wave, brushless, pulse DC motor. The motor 14 includes three windings 202a, 202b, and 202c that are tied together at one end. In versions of this invention specifically designed as a cordless, battery operated powered surgical tool, the motor 14 is capable of being driven by a battery 18 capable of providing DC pulses between 8 and 15 Volts potential and at a current of between 2 and 40 Amps depending on the load being driven. In more preferred versions of the invention, the motor 14 is driven by pulses having a potential of 9.6 Volts.

In some preferred versions of this invention the motor 14 is formed with a lamination stack with externally, outwardly facing teeth, not illustrated. This feature of the motor 14 facilitates the automated wrapping of the windings 202 around the lamination stack during the assembly of the motor.

Figure 8:
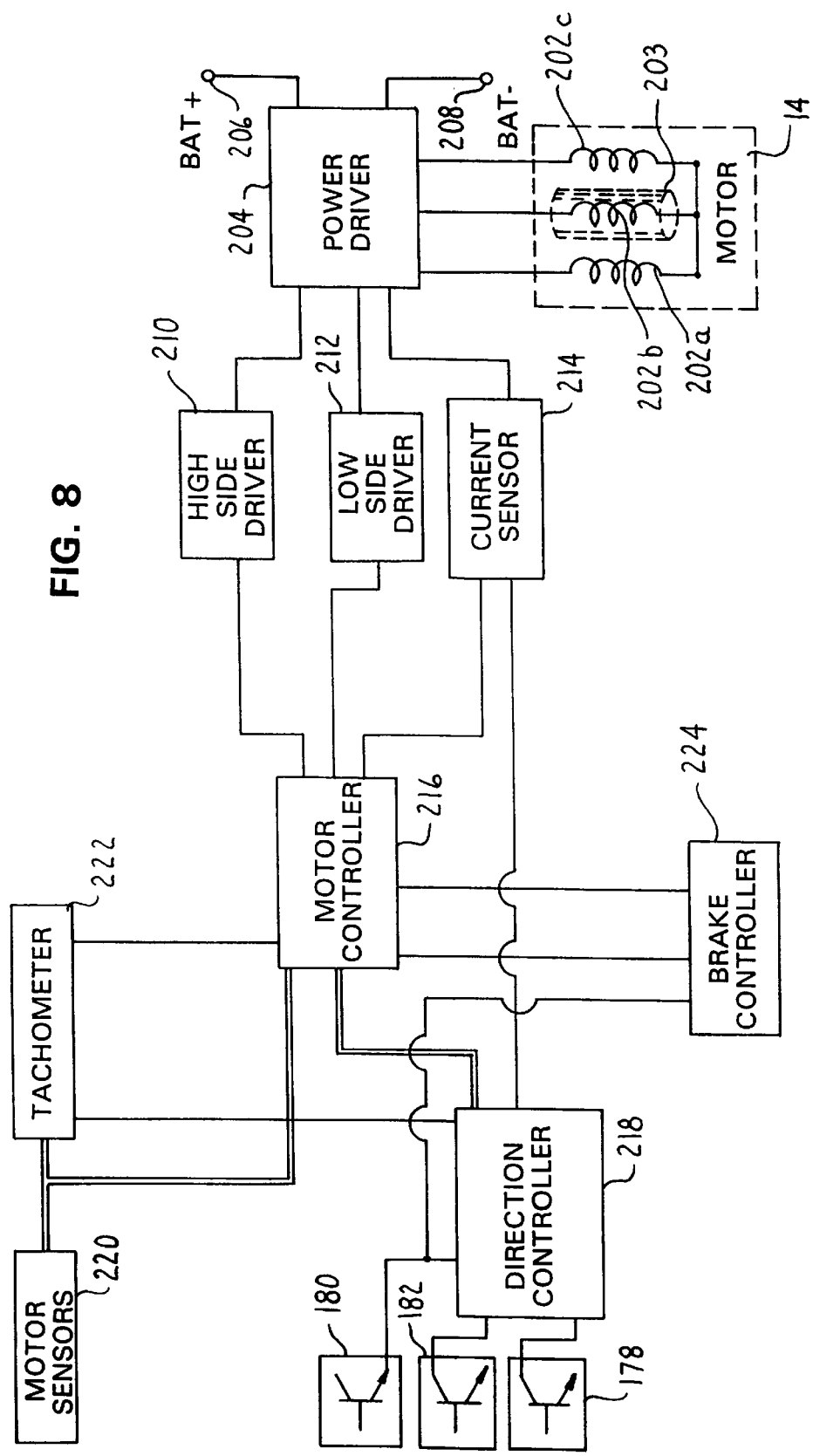
FIG. 8 is a block diagram of the major elements of the motor control circuit.
Figure 9:
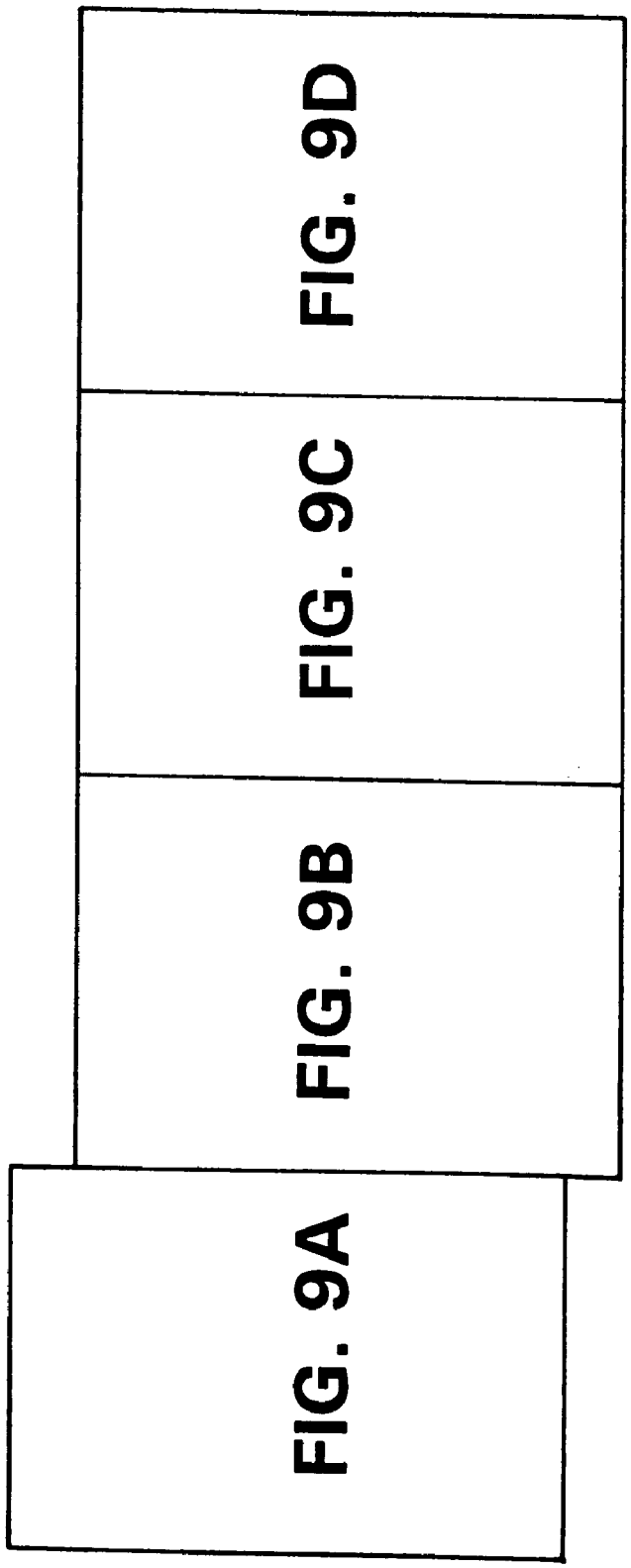
FIG. 9 is a blueprint depicting how
Figure 9A:
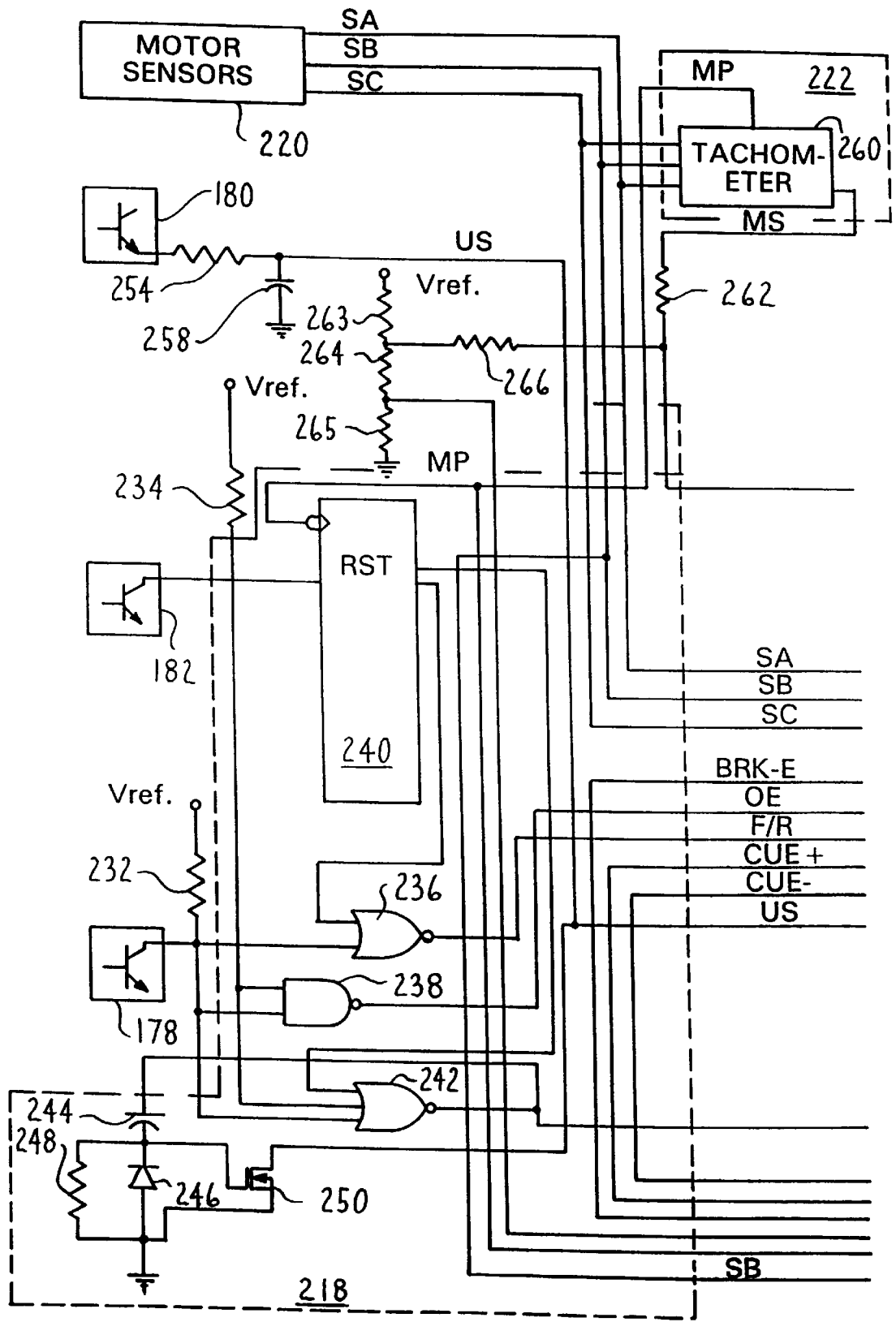
FIGS. 9A, 9B, 9C and 9D are assembled together to form a schematic diagram of components forming one particular motor control module.
Figure 9B:
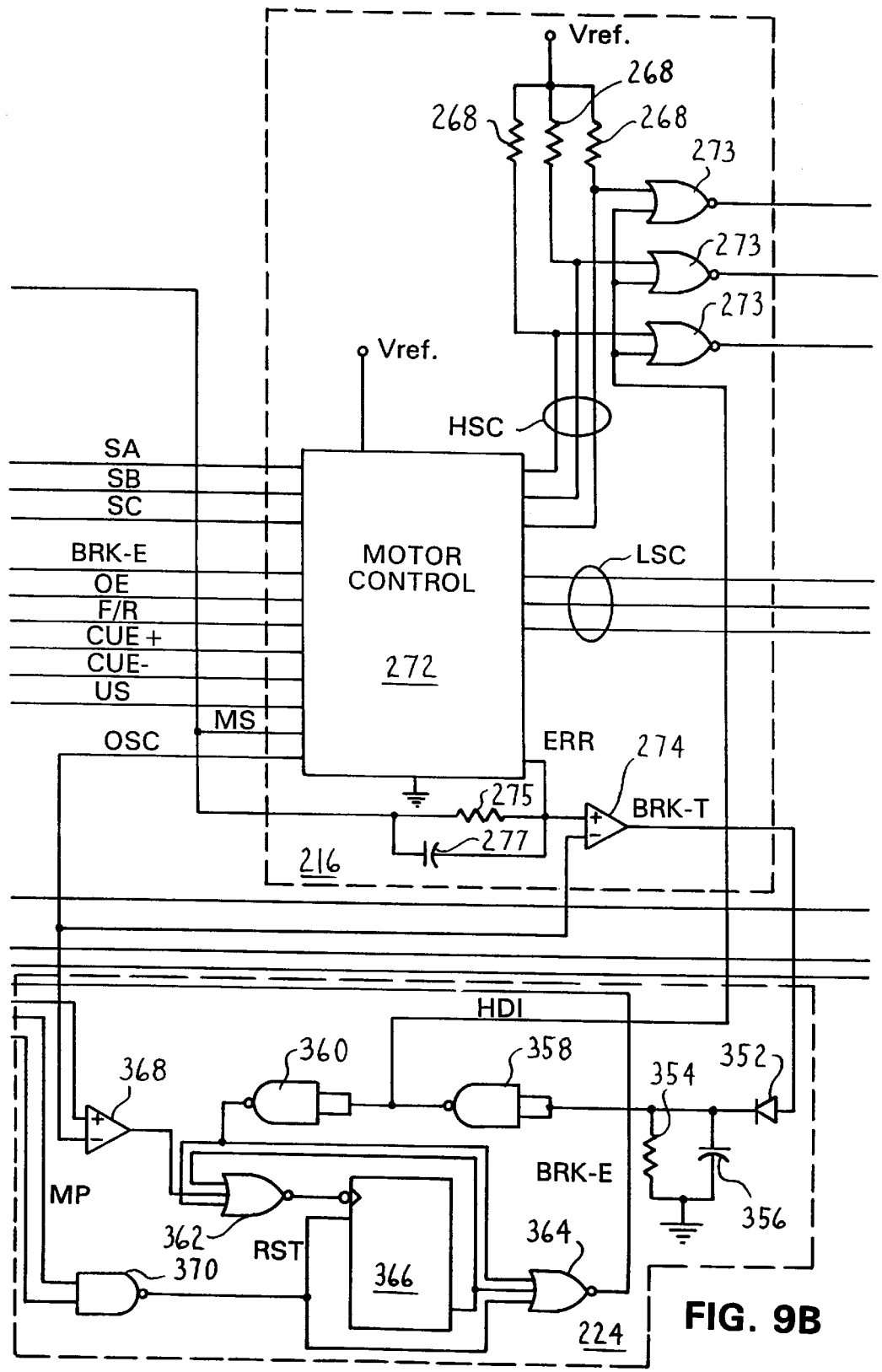
Figure 9C:
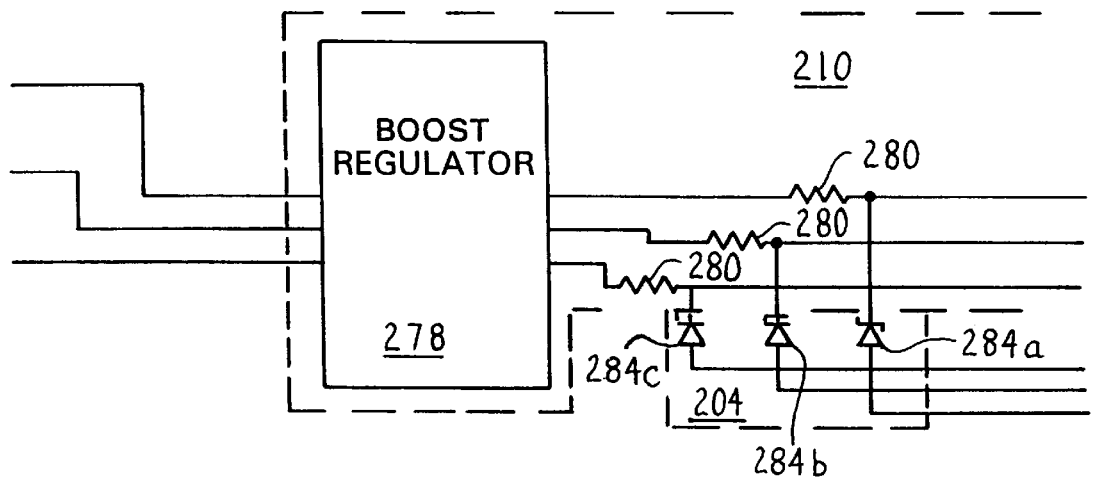
Figure 9C:
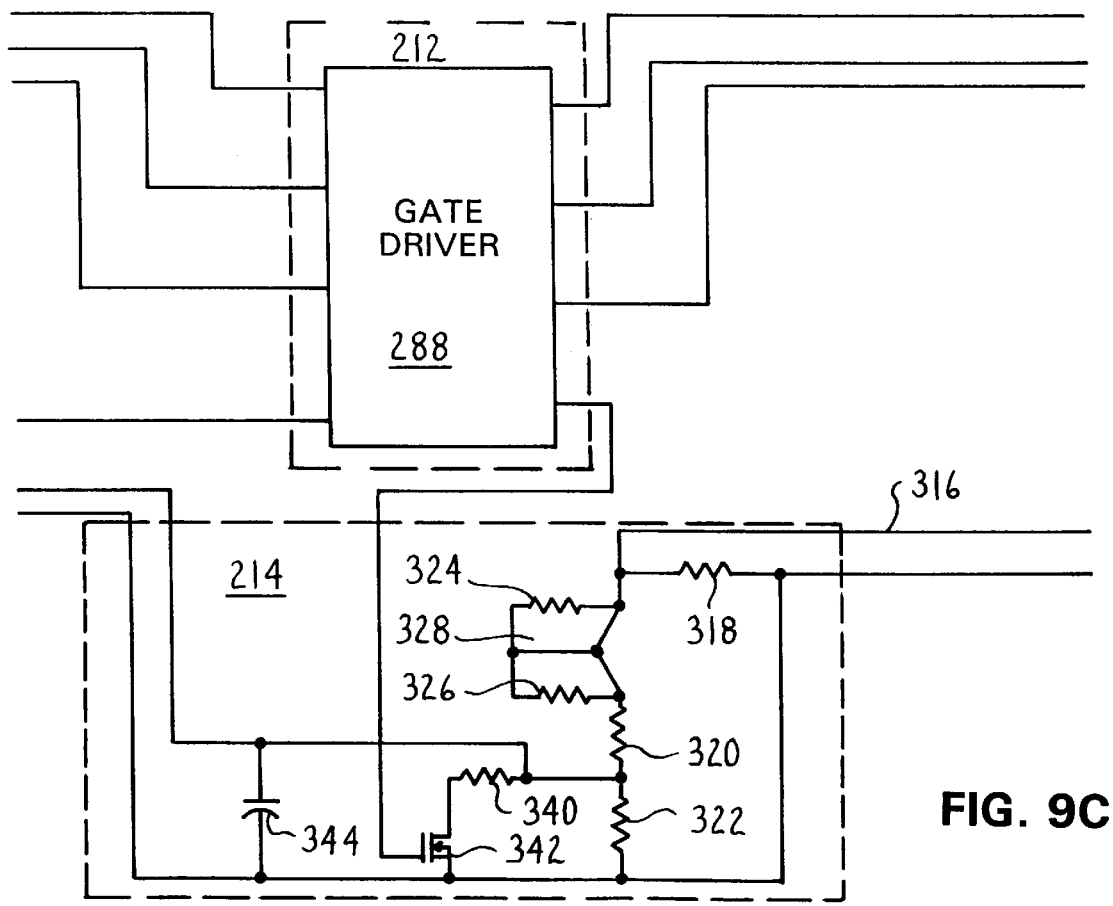
Figure 9D:
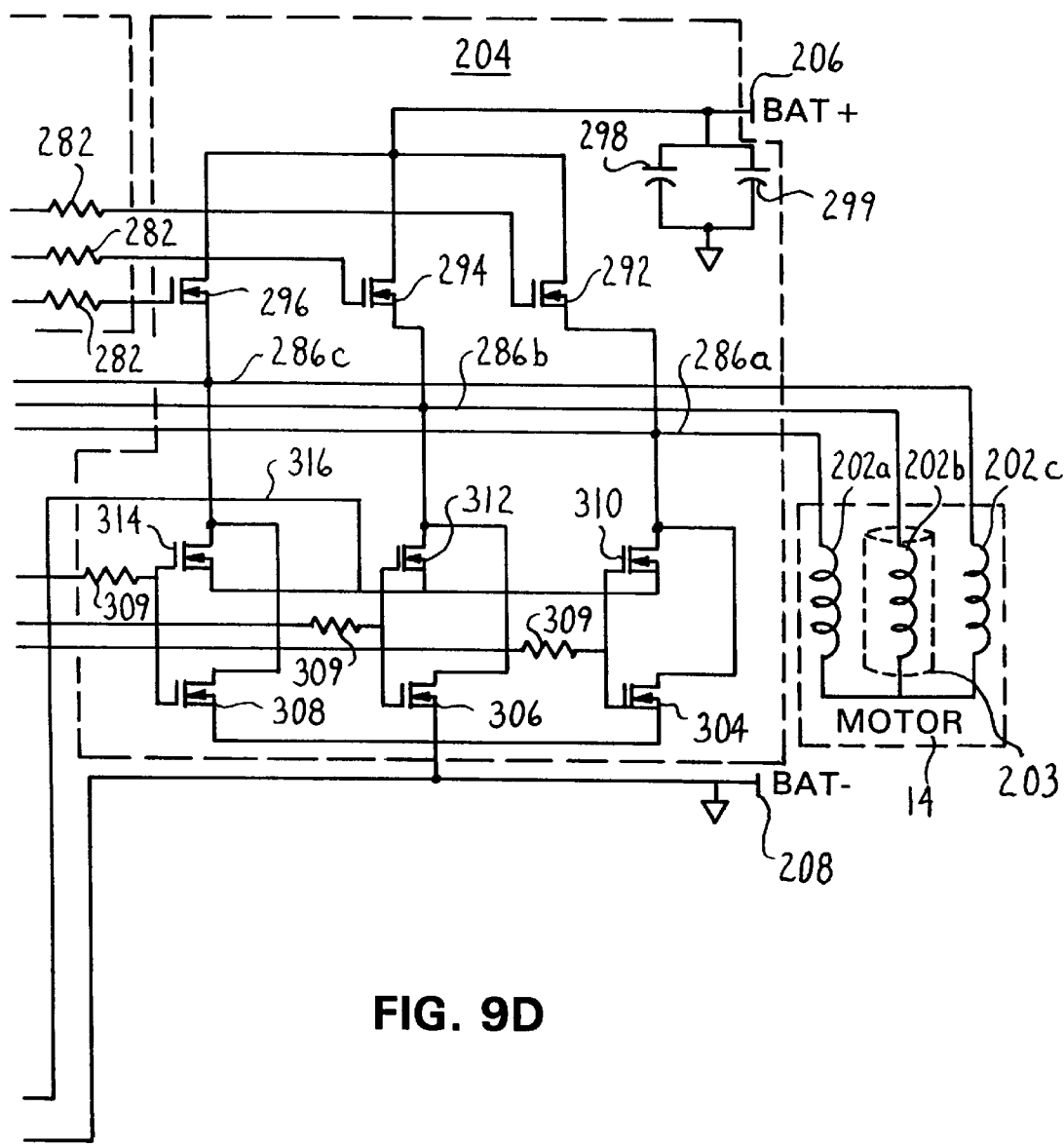

Motor 14 also includes a magnetized rotor 203, illustrated diagrammatically in FIG. 8. In some preferred versions of the drill unit 10 of this invention, in order to minimize vibrations when the motor 14 is driven in oscillatory rotation, the outer diameter of the rotor 203, the portion forming the rotor magnets, is no greater than 1.0 inches. In more preferred versions of the invention, the outer diameter of the rotor 203 is 0.6 inches or less.

The motor controller module 22 includes a number of individual circuits that collectively apply DC signals at appropriate pulse rates to the motor windings 202. The potential from the battery 18 is applied to the windings 202 through a power driver circuit 204 connected directly to the windings. The power driver circuit 204, in addition to being connected to the motor windings 202, is connected to the positive and negative terminals of the battery 18 represented respectively by terminals 206 and 208. During the commutation period for a specific winding, for example, winding 202a, the power driver circuit 204 ties winding 202a to the positive battery terminal 206. Also during that commutation period, the power driver circuit 204 rapidly opens and closes the connection between another one of the windings in this example either winding 202b or winding 202c, to the negative battery terminal 208. Thus, during each commutation period for a particular winding, pulsed DC signals are applied through two of windings in order cause the rapid development and collapse of the magnetic field around the windings used to actuate the motor rotor 203. In the aforesaid example, the field would be developed around windings 202a and 202b or windings 202a and 202c.

A high side driver circuit 210 is connected to the power driver circuit 204 for applying the signals required to cause the switching needed to connect the windings 202 to the positive battery terminal 206. A low side driver circuit 212 is connected to the power driver circuit 204 for applying the signals required to cause the switching need to connect the windings 202 to the negative battery terminal 208.

A current sensor circuit 214 is also connected to the power driver circuit 204. The current sensor circuit monitors the current through the motor windings and generates a CUR+ signal which is a volts/amp signal representative of the current drawn by the motor. The CUR+ signal is then supplied to a motor controller circuit 216. The motor controller circuit 216, in turn, determines which windings 202a, 202b or 202c are to be energized and the rate at which the windings are to be energized.

The motor controller circuit 216 receives input signals from a number of sources in addition to the current sensor circuit 214. Based on these input signals, the motor controller circuit 216 generates commands to the high and low side driver circuits 210 and 212, respectively, to cause the appropriate windings 202*a*, 202*b* or 202*c* to be tied across the battery 18 at the appropriate on/off duty cycle. Also, depending on the state of the input signals, the motor controller circuit 216 can command that each winding 202*a*, 202*b* and 202*c* be tied to ground. This causes a braking electromotive force to be generated around the motor rotor 203 so as to foster the deceleration of the motor 14.

The majority of the input signals applied to the motor controller circuit 216 originate from a direction controller circuit 218. The direction controller circuit 218 receives as input the signals generated by the Hall effect sensors 178, 180 and 182 integral with the motor controller module 22. Hall effect sensor 178, the sensor that monitors the position of left magnet 39, generates an output signal indicating if the motor 14 is to be driven in forward or oscillatory rotation. Hall effect sensor 182, the sensor that monitors the position of right magnet 41, generates an output signal indicating if the motor 14 is to be driven in reverse or oscillatory rotation. Hall effect sensor 180, the sensor that monitors the position of center magnet 40, generates an output signal indicating the speed at which the motor is to be driven.

Based on the states of the sensor signals, as well as other signals to be described hereinafter, the direction controller circuit 218 generates signals to the motor controller circuit 216 that inform the motor controller circuit of the direction in which the motor 14 should be driven and the speed at which the motor should rotate. Also, when the motor 14 driven in oscillatory rotation, the direction controller circuit 218 selectively regulates the volts/amp ratio upon which the current sensor circuit 214 basis the CUR+ signal applied to the motor controller circuit 216.

The energization of the motor 14 is also regulated based on the rotational state of the motor. In the described version of the invention, the basic motor monitoring is performed by a set of motor sensors 220. In some versions of this invention, motor sensors 220 are Hall effect sensors located adjacent the windings 202. Each sensor 220 generates pulse signals as a function of the proximity of the magnetic field of the rotor 203 relative to the sensor.

The signals generated by the motor sensors 220 are applied to the motor controller circuit 216 and a tachometer circuit 222. The tachometer circuit 222 generates output signals representative of motor state. These output signals from the tachometer circuit 222 are then applied to the motor controller circuit 216 and the direction controller circuit 218 as input signals. As will be described hereinafter, the motor controller circuit 216 and the direction controller circuit 218 generate their own control signals based on these motor state signals.

The motor controller module 22 of this invention also includes a brake controller circuit 224. The brake control circuit 224 monitors some of the signals generated by the motor controller circuit 216. Based on this signal monitoring, the brake controller circuit 224 selectively generates a BRAKE-ENABLE (BE) signal to the motor controller circuit 216 so as to cause the motor controller circuit to initiate the braking of the motor 14.

Not shown, but found in many motor controller modules 22 is a voltage regulator. The voltage regulator is connected to the battery 16 and is used to boost the battery voltage to a level needed to energize the individual signal processing components forming the motor control module 22. For example, some voltage regulators are used to provide a +12 V Vcc voltage. One such voltage regulator can be assembled with an MAX734C/D DC-to-DC voltage converter chip manufactured by Maxim. The Vref voltage upon which many of the signal comparisons described hereinafter are based is supplied by the motor controller circuit 216.

FIGS. 9A, 9B, 9C and 9D, when assembled together, form a schematic diagram of the primary components of the motor controller module 22 described above with reference to FIG. 8. The Hall effect sensors 178, 180, and 182 employed to monitor the state of the trigger assembly magnets 39, 40, 41, respectively are depicted as bi-polar transistors. The signals produced by the Hall effect sensors 178–182 are applied to the direction controller circuit 218. Specifically, the collectors of Hall effect sensors 178 and 182, the sensors employed to monitored the desired forward/ reverse/oscillate state of the motor 14, are connected to separate pull-up resistors 232 and 234, respectively. The opposed end of each pull-up resistor 232 and 234 is tied to the Vref voltage source. Hall effect sensors 178 and 182 are thus configured so that when the magnets 39 and 41 associated with each sensor are in their at-rest state, the sensors produce a relatively high impedance output. Consequently, when each magnet 39 and 41 is in this state, high signals appear at the junctions of each sensor 178 and 182 with its associated pull-up resistor 232 and 234, respectively.

In the described embodiment of the invention, the trigger assembly is configured so that each magnet 39, 40 and 41 can travel approximately 350 mils. Hall effect sensors 178 and 182 are configured so that once the associated magnet 39 or 41 is displaced approximately 65 to 165 mils from its at-rest position, the sensor will generate a signal sufficient to cause the signal at the pull-up resistor junction to transition to a low signal that can be detected by the downline components.

The signal present at the collector/pull-up resistor junction of sensor 178, the sensor associated with the magnet 39 actuated in response to a forward or oscillate motor command, is applied to one input of a NOR gate 236. Gate 236 produces a FORWARD/REVERSE (F/R) signal that is applied to the motor controller circuit 218.

The signal present at the pull-up resistor junction of sensor 178 is also applied to one-input of a NAND gate 238. NAND gate 238 selectively generates an OUTPUT-ENABLE (OE) signal to the motor controller circuit 216. NAND gate 238 only generates the OUTPUT-ENABLE signal if one of the Hall effect sensors 178 or 182 generate a signal indicating the complementary trigger assembly magnet 39 or 41 has been generated. This feature of the driver controller circuit 218 thus prohibits the inadvertent actuation of the motor controller circuit 216 and the resultant unintended actuation of the motor 14 if neither trigger switch 26 nor trigger switch 28 have been depressed.

The signal present at the collector/pull-up resistor junction of sensor 182, the sensor associated with the magnet 41 actuated in response to a reverse or an oscillate motor command, is applied to the second input of NAND gate 238.

The output signal from sensor 182 also functions as a RESET (RST) signal that is applied to a counter 240 that also forms part of the direction controller circuit 218. In the depicted version of the invention, counter 240 is a falling-edge triggered counter. The counter 240 receives clock pulses the signals generated by the tachometer circuit 222 that are representative of the incremental rotation of the motor rotor 203. A first one of the output signals generated by the counter 240 is applied to the second input of NOR gate 236.

A second output signal from the counter 240, a signal having twice the frequency of the first output signal, is applied to one of the inputs of a three-input NOR gate 242. The other two input signals applied to NOR gate 242 are the output signals produced by the forward and reverse Hall effect sensors 178 and 182, respectively. The output signal from NOR gate 242 is branched to a ground through a series-connected capacitor 244 and a forward-biased diode 246. A resistor 248 is connected in parallel across the diode 246. A n-channel FET 250 is also tied across diode 246. More specifically the drain and gate of FET 250 are tied respectively to the anode and cathode of diode 246. For purposes to be explained hereinafter, the capacitance of capacitor 244 and the resistance of resistor 248 are selected so that each time the output from NOR gate transitions from low to high, a pulse signal is placed across the gate of FET 250 sufficient to close the FET for a period ranging from 10 to 75 msec. In more preferred versions of the invention the pulse is applied across the gate of FET 250 to close the FET for approximately 60 msec.

The center-position Hall effect sensor, Hall effect sensor 180, produces an output signal representative of the user-selected rotational speed of the motor 14. The output signal from Hall effect sensor 180 is taken off the sensor's emitter through a resistor 254. A capacitor 258 is connected between the end of resistor 254 distal from the sensor 180 and ground. The signal present at the junction of resistor 254 and capacitor 258 is an analog USER-SPEED (US) signal representative of the rotational rate at which the motor 14 should be driven. The conductor over which the USER-SPEED signal travels is connected to both the motor controller circuit 216 and to the drain of FET 250.

In many preferred versions of the invention, Hall effect sensor 180 is a bipolar sensor responsive to both positive and negative gaussian fields that are present in the vicinity of the sensor. Magnet 40 is formed out of the two opposed magnets 114 and 116 in order to enhance the sensitivity of the sensor 180. In one preferred version of the invention, magnet 40 has a pre-travel displacement of approximately 165 mils from its at-rest position before the sensor 180 causes a shift in the USER-SPEED signal. Magnet 40 then travels approximately a 75 mil distance, referred to as the variable speed travel, during which the output of sensor 180 will cause a complete transition of the USER-SPEED signal. The remaining, approximately 75 mils, of the travel of magnet 40 will not cause any additional change in the output of the sensor 180 or the USER-SPEED signal. The movement of the magnet 40 in this region, as well as of the associated magnet(s) 39 and/or 41 is referred to as post-travel movement.

The tachometer circuit 220 essentially consists of a single tachometer chip 260. One suitable tachometer chip 260 is the MC33039 tachometer chip manufactured by Motorola. The tachometer chip 260 receives as input signals the pulse signals produced by the motor sensors 220, identified as signals SA, SB and SC. In response to the signals produced by the motor sensors 220, tachometer chip 260 produces variable frequency DC pulses, a MOTOR-PULSE (MP) signal, representative of motor speed. The MOTOR-PULSE signal is applied to the direction controller circuit counter 240 to function as the counter clock signals. The MOTOR-PULSE signal generated by the tachometer chip 260 are also applied to the brake control circuit 224.

The tachometer chip 260 also produces a pulse DC MOTOR-SPEED (MS) signal representative of motor speed. The MOTOR-SPEED signal is a pulse signal that is always on for a fixed unit of time in a variable time period that varies inversely with measured motor speed. The MOTOR-SPEED signal is applied to the motor controller circuit 216 through a resistor 262. In the illustrated version of this invention, a small offset voltage is applied to the conductor over which the MOTOR-SPEED signal is applied to the motor controller circuit 216. The offset voltage is taken off a voltage divider which consists of three series connected resistors 263, 264 and 265. Resistor 263 is connected to the Vref voltage source and resistor 265 is connected to ground. The offset voltage is taken off the junction of resistors 263 and 264 and is applied to the motor controller circuit through a resistor 266. This offset voltage is applied to the MOTOR-SPEED signal so that an analog, integrated form of the MOTOR-SPEED signal can be accurately compared to the user-selected USER-SPEED signal.

The motor controller circuit 216 includes a motor control chip 272. One particular motor control chip 272 from which invention has been constructed is the MC33035 brushless DC motor control chip manufactured by Motorola. The motor control chip 272 receives as input signals the SA, SB and SC pulse signals generated by the motor sensors 220, the OUTPUT-ENABLE, the FORWARD/REVERSE and the USER-SPEED signals produced by the direction controller circuit 218 and the MOTOR-SPEED signal generated by the tachometer chip 260. As will be discussed hereinafter, the motor control chip 272 also receives the BRAKE-ENABLE (BRK-E) signal from the brake controller circuit 224 and the CUR+ and CUR signals representative of the current drawn by the motor 14 from the current sensor circuit 214.

In response to receiving the foregoing input signals, the motor control chip 272 generates the signals that result in the motor windings 202 being selectively tied to the battery 18 in order to control the rotational movement of the motor 14. The primary signals motor control chip 272 generates are a set of HIGH-SIDE-CONTROL (HSC) signals and a set of LOW-SIDE-CONTROL (LSC) signals. The HIGH-SIDE-CONTROL signals are applied to the high side driver circuit 210 to cause the windings 202 to be individually connected to the positive battery terminal 206.

The individual HIGH-SIDE-CONTROL signals, which are asserted high, are actually applied to three identical pull-up resistors 268 that are connected to receive the Vref voltage. The signals present at the junctions of resistors 268 and the HIGH-SIDE-CONTROL conductors extending from motor control chip 272 are applied to the input terminals of three separate NOR gates 273 also part of the motor controller circuit 216. The second input to each NOR gate 273 is a HIGH-DRIVE-INHIBIT (HDI) signal that is selectively asserted by the brake controller circuit 224. The output signals from NOR gates 273 are applied to separate inputs of the high side driver control circuit 210.

The LOW-SIDE-CONTROL signals are applied to the low side driver circuit 212. Normally, at any given instant only a single LOW-SIDE-CONTROL signal is asserted to tie a single one of the windings 202a, 202b or 202c to the negative battery terminal. However, when the motor control chip 272 receives a BRAKE-ENABLE signal, the chip 272 will assert LOW-SIDE-CONTROL signals so as to tie each winding 202a, 202b and 202c to ground.

The motor control chip 272, in addition to generating the signals required to tie the motor windings 202 to either a voltage source or ground, also generates a number of signals used by the other components forming the motor control module 22. The motor control chip 272 is the source of the Vref voltage reference signal. The motor control chip also generates a fixed frequency, sawtooth profile OSCILLATOR (OSC) signal. (Resistor and capacitor used to establish the frequency of the OSCILLATOR signal not shown.)

Motor control chip 272 also generates an analog ERROR (ERR) signal representative of the difference between the measured motor speed and the speed at which the user actually wants the motor to be driven. The ERROR signal is based on the difference in magnitude between the USER-SPEED signal and the MOTOR-SPEED signal. In the depicted version of the invention, the motor controller chip 272 has an internal high-gain op amp, not illustrated, to which the MOTOR-SPEED and USER-SPEED signals are applied as separate inputs. The out-put of this op amp, the ERROR signal, is supplied as feedback to the motor control chin 272 input to which the MOTOR-SPEED signal is applied. The feedback of the ERROR signal is through a resistor 275. A capacitor 277 tied across resistor 275 integrated the pulse signals forming the tachometer-generated MOTOR-SPEED signal to present the analog, integrated form of the MOTOR-SPEED signal to the appropriate input on the motor control chip 272. In some preferred versions of this invention, the gain of the op amp that generates the ERROR signal is between 10 and 100, in more preferred versions of the invention, the gain is approximately 20.

The motor control circuit 216 also includes a comparator 274. Comparator 274 receives at its non-inverting input the ERROR signal from motor control chip 272. The OSCILLATOR signal is applied to the inverting input of comparator 274. During positive phases of the OSCILLATE signal, whenever the ERROR signal exceeds a certain level, the comparator 274 asserts a BRAKE-TRIGGER (BRK-T) signal to the brake controller circuit 224. In the described version of the invention the BRAKE-TRIGGER signal is asserted low.

The high side driver circuit 210 selectively applies an overdrive voltage to the individual high-side switches integral with the power driver circuit 204 in order to selectively tie the motor windings 202a, 202b and 202c to the positive batter terminal 206. The high side driver includes a boost regulator 278 that is primarily responsible for providing individual DC pulses that are boosted to a potential +12 V above the potential across the battery 18. One suitable boost regulator 278 is the MAX620C/D boost regulator manufactured by Maxim. Boost regulator 278 has three inputs each of which receives a different one of the three output signals produced by the individual motor controller circuit NOR gates 273. Depending on which NOR gate 273 asserts a high signal, the boost regulator 278 generates a gate signal to a specific high-side FET internal to the power driver circuit 204 as will be discussed hereinafter. The individual gate signals are applied to each FET through three pairs of series connected resistors, each pair identified as resistor 280 and resistor 282.

The low side driver circuit 212 generates the high current pulses required to switch the low side FETs internal to the power driver circuit 204 as will be discussed hereinafter. In the depicted version of the invention, the low side driver circuit consists of an input programmable gate driver chip 288 such as an TC4469 manufactured by Telcom. The gate driver chip 288 is capable of generating high current, approximately 1.5 A, pulses that can be applied to FETs in order to rapidly force the FETs in and out of conduction. This rapid switching is needed because, during operation of the drill unit it is often necessary to selectively connect and disconnect the motor windings 202 to the negative battery terminal 208. Ideally the rise and fall times of the FETs switched by the drive chip 288 should be 100 nanosec or less.

The gate driver chip 288 has three input terminals at which the individual LOW-SIDE-CONTROL signals from the motor control chip 216 are received. Depending on which LOW-SIDE-CONTROL signal is received, gate driver chip 288 generates a high-current signal over one of three output terminals to one of the FETs internal to the power driver circuit 204.

Gate driver chip 288 has a fourth input terminal over which the signal produced by driver controller circuit NOR gate 242 is received. Whenever NOR gate 242 asserts a low signal, the gate driver chip 288 asserts a fourth high current pulse out of a fourth output terminal to the current sensor circuit 214 for a purpose to be explained hereinafter. The application of a high signal to the fourth input terminal of gate driver chip 288 thus causes the chip to negate the output of a high current pulse. Thus, the application of a high signal to the fourth terminal of the gate driver chip 283 causes an opposite response than what occurs when a high signal is applied to one of the first three input terminals of chip 288.

The power driver circuit 204 has a num ber of FETs that are connected to the winding conductors 286 which connect each winding 202a, 202b or 202c to either the positive or negative battery terminal 206 or 208, respectively. Three n-channel FETs 292, 294, and 296 are tied between the positive battery terminal 206 and the individual conductors 286a, 286b and 286c, respectively, for selectively applying the battery voltage to an individual windings 202a, 202b or 202c. The gate of each FET 292, 294 and 296 is connected to a separate one of the output terminals of the boost regulator 278 through an individual one of the series-connected resistors 280 and 282.

The power driver circuit 204 further includes three identical zener diodes 284a, 284b 284c. The anodes of diodes 284a, 284b and 284c is connected to the source of a separate one of the FETs 292, 294 and 296 respectively. The cathode of each diode 284a, 284b and 284c are connected to the gate of the associated FET 292, 294 and 296, respectively through the resistor 282 to which the gate is connected. Each diode 284 prevents burn out of the associated FET 292, 294 or 296 in the event gate-tosource voltage across the FET exceeds a selected voltage, in some versions of the invention, approximately 20 volts.

Two parallel connected, grounded capacitors 298 and 299 are connected between the positive battery terminal 206 and FETS 292, 294 and 296. Capacitors 298 and 299 provide high pass filtering of the voltage applied from the battery 18 in order to minimize the application of uneven voltages to the windings 202.

Three n-channel FETS 304, 306 and 308 selectively tie the motor windings 202 to the negative battery terminal 208. Each FET 304, 306 and 308 is connected to a separate one of the windings 202a, 202b and 202c, respectively, through a separate one of the conductors 286a, 286b and 286c, respectively. The gates of each FET 304, 306 and 308 are each connected to an individual one of the output terminals of the gate driver chip 288. The gates of FETs 304–308 are connected to the gate driver chip 288 through separate, identical resistors 309.

Connected in parallel with FETs 304, 306 and 308 to conductors 286 are three additional n-channel FETS 310, 312, and 314, respectively. The gate of each FET 310, 312 and 314 receives the signal applied to the gate of the FET 304, 306 or 308, respectively, with which it is paired. FETs 310–314 are thus turned on only when their complementary FETs 304–308 are placed in a like state in order to monitor the current flow through the associated winding 202a, 202b or 202c. The sources of FETs 310, 312 and 314 are tied to a common conductor 316 that is connected to the current sensor circuit 214.

The current sensor circuit 214 includes a resistor 318 through which the current through conductor 316 is forced to ground. Current sensor circuit 214 includes a resistor bridge formed of series connected resistors 320 and 322. One end of the resistor 320-resistor 322 bridge is tied between the junction of the FETs 310–314 and resistor 318. The opposed end of the resistor bridge is tied to ground (the negative battery terminal 208). A pair of parallel connected resistors 324 and 326 as well as a conductor 328 are connected between conductor 316 and the bridge formed by resistors 320 and 322. A resistor 340 and an n-channel FET 342 are connected in parallel across bridge resistor 322. The gate of FET 342 is connected to the gate driver chip 288 to receive the high current output pulse generated in response to the assertion of the NOR gate 242 high signal.

Resistor 340 has a resistance that is substantially less than that of resistor 322. In some versions of the invention resistor 322 has a resistance approximately 30 times greater than that of resistor 340. Consequently, when FET 342 is closed the volts/amp ratio upon which the CUR+ signal is based is substantially less than the volts/amp ratio when the FET 342 is open and resistor 340 is no longer tied to ground.

The signal present at the junction of resistors 320, 322 and 340 is applied to the motor control chip 272 as the CUR+ sensed current signal. The ground conductor tied to the negative battery terminal, conductor not identified, is applied to the motor control chip 272 as a CUR− signal. Hereinafter, the signal out of the current sensor circuit will continue to be referred to as the CUR+ signal. A capacitor 344 connected across resistor 340 and FET 342 removes high frequency spikes from the CUR+ signal.

The brake controller circuit 224 includes a diode 352 to which the BRAKE-TRIGGER signal from comparator 274 is applied. A resistor 354 and a capacitor 356 are connected in parallel between the cathode of diode 252 and ground. Resistor 354 and capacitor 356 are selected to hold the signal at the cathode of diode 352 high in the event the BRAKE-TRIGGER signal, a low-asserted signal, is momentarily asserted.

The signal present at the cathode of diode 352 is applied to both inputs of a NAND gate 358 so that the gate functions as an invertor. The output signal from NAND gate 358 is applied to the second inputs of the motor controller circuit NOR gates 273 as the HIGH-DRIVE-INHIBIT signal. The output signal from NAND gate 358 is also applied to both inputs of a second NAND gate 360 so that the signal is inverted back into the state it was in before application to the first NAND gate 358. In some versions of the this invention, NAND gates 358 and 360 are Schmitt trigger gates so as to substantially reduce signal bounce of the output signal.

The output signal from NAND gate 360 is applied to separate inputs of first and second three-input NOR gates 362 and 364, respectively. The output signal of the first NOR gate, NOR gate 362, is applied to the clock input of a counter 366, also part of the brake controller circuit. As a second input, NOR gate 362 receives the slowest cycling, high count, output signal from the counter 366. As can be seen, in this version of the invention counter 366 is a trailing edge triggered counter. A comparator 368 supplies the third input signal to NOR gate 362. The input to the non-inverting input to the comparator 368 is a reference voltage. In this version of the invention, that reference voltage is taken off the junction between resistors 264 and 265. The OSCILLATOR signal from motor control chip 272 is applied to the inverting input of comparator 368.

A NAND gate 370 supplies a reset signal to counter 366 as well as the second input signal to NOR gate 364. A first input to NAND gate 370 is the MOTOR-PULSE signal from the tachometer chip 260. The second input to the NAND gate 370 is the signal received from one of the motor sensors 220.

The third input to NOR gate 364 is the aforementioned slowest cycling count signal asserted by counter 366. The output signal asserted by NOR gate 364 is the BRAKE-ENABLE signal that is applied to the motor control chip 272.

The drill unit 10 forming the cordless, battery operated powered surgical tool unit of this invention is used like conventional drill units. Prior to the drill unit 10 being used for a specific medical procedure, medical personnel secure the appropriate cutting attachment to the motor rotor 203. The surgeon then uses the tool by actuating the appropriate trigger switch 26 or 28 to cause either forward or reverse motion of the motor 16. The actuation of the trigger switch 28 or 26 causes the like actuation of the associated direction left or right magnet 39 or 41, respectively. Since the carrier 106 holding the center magnet 40 is configured to moved by the carriers 88 and 90 that, respectively, hold the left and right magnets, the center magnet 40 is displaced with the like displacement of either the left or right magnet.

The displacements of magnets 39, 40 and 41 are monitored by the Hall effect sensors 178, 180 and 182, respectively which are contained in the sealed motor control module housing 150. If neither trigger switch 28 nor 26 are actuated, high signals are present at the ends of pull-up resistors 232 and 234 distal from the Vref voltage source. These signals are applied to the inputs of NAND gate 238. When the drill unit 10 is in this state, NAND gate 238 thus asserts a low, $\overline{\text{OUTPUT-ENABLED}}$ signal to the motor control chip 272. The receipt of the $\overline{\text{OUTPUT-ENABLE}}$ signal by the motor control chip 272, disables the chip so as to prevent the inadvertent application of energization voltages to the motor windings 202.

The high signal off the pull-up resistor 234 associated with Hall effect sensor 182, the sensor associated with reverse trigger switch 26, is applied to the direction controller circuit counter 240 as a RESET signal. Consequently, counter 240 asserts a low signal to the input of NOR gate 236. Nor gate 236, in turn asserts a high signal to the motor control chip 272 which is recognized by the chip 272 as a $\overline{\text{FORWARD}}$/REVERSE state $\overline{\text{FORWARD}}$/REVERSE signal. Thus, the default state for the direction controller circuit 218 is to generate a $\overline{\text{FORWARD}}$/REVERSE state, signal a reverse direction signal, to the motor control chip 272.

In the event trigger switch 28, the forward rotation switch, is depressed, the change in signal state of the associated Hall effect sensor 178 causes the signal present at the collector of Hall effect sensor 178 to transition from high to low. This transition causes a like transition of the output signal from NAND gate 238 from $\overline{\text{OUTPUT-ENABLE}}$ to OUTPUT-ENABLE. The transition to the OUTPUT-ENABLE signal serves to enable the motor control chip 272. The low signal present at Hall effect sensor 178 is also applied to the second input of NOR gate 236. Since the first input of NOR gate 236 is likewise receiving a low signal from counter 240, the output of the gate transitions from the $\overline{\text{FORWARD}}$/REVERSE state signal to a FORWARD/$\overline{\text{REVERSE}}$ state signal. The FORWARD/$\overline{\text{REVERSE}}$ signal applied is thus applied to the motor control chip 272 which, in turn, interprets the signal as a command to actuate the motor 14 into forward rotation.

The depression of trigger switch 28 also results in a like displacement of the center magnet 40. Once magnet 40 passes out of the pre-travel region, the signal produced by the associated Hall effect sensor 180 begins to transition from a low state. This signal is applied to the motor control chip 272 as the USER-SPEED signal. The motor control chip 272, in turn, periodically asserts the HIGH-SIDE-CONTROL and LOW-SIDE-CONTROL signals at the appropriate frequency in order to cause the motor 14 to rotate at the desired speed.

In the event only the reverse direction trigger switch 26 is depressed, the signal present at the collector of Hall effect sensor 182 transitions from high to low. Consequently, the output from the NAND gate 238 transitions from OUTPUT-ENABLE to OUTPUT-ENABLE as described with respect to the actuation of trigger switch 26. Since, in this state, the input signal from the forward-rotation command Hall effect sensor 178 remains constant, high, NOR gate 236 will continue to assert the default FORWARD/REVERSE signal to the motor control chip 272. The motor control chip 272, in turn, recognizes the receipt of the FORWARD/REVERSE signal as a command to cause the reverse rotation of the motor 14. The motor windings 202 are thus selectively energized at the appropriate rate to cause the motor 14 to rotate at the appropriate reverse speed based on the extent of the variable speed travel of the magnet 40.

When either only the forward trigger switch 28 or only the reverse trigger switch 26 is depressed, the signal from the Hall effect sensor 178 or 182 associated with the non-actuated switch will continue to assert a high signal to NOR gate 242. Thus, as long as only a single trigger switch 26 or 28 is depressed, NOR gate 242 will continue to assert a low signal. The low signal from NOR gate 242 will be applied to the fourth input of gate driver 288 and result in the actuation of a high current output signal from the gate driver. This high current output signal is applied directly to the gate of FET 342 so as tie the FET to ground. Consequently, as long as drill unit 10 is actuated to operate in a single rotational direction, current sensor circuit 214 will apply a CUR+ signal to the motor control chip 272 based on the lower of the two volts/amp ratios.

In the event the surgeon wants to drive the motor 14 in oscillatory rotation, he/she simultaneously depresses both trigger switches 26 and 28. This action causes a low signal to appear at the collectors of both Hall effect sensors 178 and 180. NAND gate 238 asserts the OUTPUT-ENABLE signal as previously discussed. The low signal present from Hall effect sensor 178, the forward direction sensor, is again applied to one input of NOR gate 236 so as to cause the gate to assert the FORWARD/REVERSE signal. The low signal from Hall effect sensor 182 that is applied to counter 240 as a RESET signal that effectively enables the count cycle of the counter.

The low signals from both Hall effect sensors 178 and 182 are also both applied to two of the three inputs of NOR gate 242. Thus, as discussed below, it should be recognized that NOR gate 242 in this state serves to invert its third input signal, the second output signal generated by counter 240.

As discussed above, when the trigger switches 26 and 28 are actuated to cause the motor 14 to oscillate, initially a FORWARD/REVERSE signal is applied to the motor control chip 272 from NOR gate 236. Since the counter 240 is enabled, the MOTOR-PULSE signal generated by the tachometer chip 260, and applied to the-counter as a clock signal, cause the count outputted by the counter to advance. After a given number of received individual MOTOR-PULSE signals are received by counter 240, the first signal from the counter transitions from low to high as represented by the timing diagram FIG. 10A. In some preferred versions of the invention, the counter 240 is programmed to transition the first output signal after MOTOR-PULSE signal pulses indicative of between 270° to 720° of motor rotation have been received. In more preferred versions of the invention, the counter 240 transitions the first output signal after MOTOR-PULSE signal pulses indicative of approximately 417° of motor rotation have been received.

The first output signal from counter 240 is the signal that is applied to the second input of NOR gate 236. Consequently, NOR gate 236 transitions from asserting the FORWARD/REVERSE state signal to assert the FORWARD/REVERSE state signal as is represented by FIG. 10B. Thus, the direction signal asserted by the direction controller circuit 218 and applied to the motor controller circuit 216 changes state. This signal state change, in turn, causes the motor controller circuit 216, and in particular the motor control chip 272, to assert signals that cause the motor 14 to reverse its direction of rotation.

As represented by FIG. 10C, the second output signal from counter 240 clocks at a frequency twice that of the rate at which the first output signal clocks. Thus, simultaneously with the application of the first low-to-high signal transition of the first output signal from counter 240, the second output signal from counter 240 undergoes a high-to-low transition. The second output signal from the counter is applied to the third input of NOR gate 242. Since at the time prior to this signal transition, the second output signal was in a high state, NOR gate 242 was asserting a low signal as is represented by FIG. 10D. Consequently, the transition of the second output signal from counter 240 low causes NOR gate 242 to undergo a low-to-high signal state transition. A first effect of the low-to-high signal state transition of the output of NOR gate 242 is that it causes a pulse to appear across the gate of FET 250 sufficient to momentarily tie the drain of the FET 250 to ground. Since the USER-SPEED signal generated by Hall effect sensor 180 is tied to the drain of FET 250, the USER-SPEED signal is thus momentarily forced low as is represented by FIG. 10E. Thus, at the moment the FORWARD/REVERSE signal applied to the motor control chip 272 changes state, a low, zero-speed, USER-SPEED signal is applied to the motor control chip 272.

The application of the zero-speed USER-SPEED signal to the motor control chip 272 has two effects. First, in response to the zero speed USER-SPEED signal, the motor control chip 272 at least momentarily ceases the assertion of LOW-SIDE-CONTROL signals that cause the actuation of the motor 14. This gives the motor rotor some time to slow and then stop so that the rotor can smoothly reverse the direction of rotation.

Secondly, when the zero speed USER-SPEED signal is asserted, the motor speed will inherently be greater than the desired USER-SPEED. Consequently the motor control chip 272 will generate an ERROR signal to the comparator 274 sufficient to cause the comparator to assert the BRAKE-TRIGGER signal. The assertion of the BRAKE-TRIGGER signal, in turn, results in the brake controller circuit 224 asserting the BRAKE-ENABLE signal to the motor control chip 272. The motor controller chip 272 will, in turn, generate the LOW-SIDE-CONTROL signals needed to cause the braking, the deceleration, of the motor rotor 203.

Thus, during reversal of rotation of the rotor 203, the motor control chip 272 not only negates the application of energization signals that cause the rotor to be abruptly forced into reverse rotation. The motor control chip 272 also asserts control signals that cause the rotor 203 to slow down. Thus, when the reverse direction energization signals are applied to the motor windings 202, the rotor 203 will be turning either relatively slowly or not at all so that the initial reverse motion of the rotor will not result in significant vibration-inducing mechanical shock.

A second effect of the transition of the output of NOR gate 242 from low to high is that the signal gate 242 applies to the fourth input of gate driver chip 288 also goes low. Consequently, the gate driver chip 288 ceases to assert the requisite high current gate driver signal needed to hold FET 342 closed. The opening of FET 342 causes the current sensor circuit 214 to produce the CUR+ based on the higher of the two volts/amp ratios. As a result, a larger magnitude CUR+ signal is presented to the motor control chip 272.

The motor control chip 272, upon receiving this larger CUR+ signal, in turn limits the application of energization signals to the windings so as to prevent the "apparent" measured current from not exceeding a predefined maximum current draw. Thus, at least while the signal asserted by NOR gate 242 remains low, during the first part of the reverse direction energization cycle when the motor 14 is being driven in the oscillatory mode, the motor control chip 272 further only asserts control signals that limit the current the drawn by the motor 14.

Referring again to FIG. 10C, it can be seen that half way through the reverse direction cycle, the second output signal from counter 240 transitions from low back to high. As shown by FIG. 10D, this causes an opposite change in the state of the signal asserted by NOR gate 242. The low signal from NOR gate 242 is applied to the gate driver 288 which, in turn, asserts the high current signal required to close FET 342. Consequently the current sensor circuit 214 returns to generating the CUR+ signal based on the lower volts/amp ratio. A lower CUR+ signal is again presented to the motor control chip 272. The motor control chip 272 is thus then able to assert the HIGH- and LOW-SIDE-CONTROL signals that accelerate the motor rotor 203 higher speeds, the accelerations that cause the motor to draw more current.

As counter 240 continues to receive additional MOTOR-PULSE signals from the tachometer chip 260, the first output signal of counter 240 will eventually transition from high back to low. Simultaneously with this transition, the second output signal from counter 240 will again transition from high back to low. Thus, as a result of the transition of the first output signal from counter 240, NOR gate 236 will transition from asserting the $\overline{\text{FORWARD/REVERSE}}$ state signal back to asserting the FORWARD/$\overline{\text{REVERSE}}$ state signal. As a result of the simultaneous transition of the second output signal from counter 240 (FIG. 10C) the signal asserted by NOR gate 242 will again transition back from low to high (FIG. 10D). This latter signal transition will cause the zeroing of the USER-SPEED signal and the switching of the magnitude of the CUR+ signal received by the motor control chip 272 as was discussed when the motor 14 under went the initial forward-to-reverse rotation direction change. These latter signal state changes thus occur when the motor 14 is being driven in oscillatory rotation and at the time the motor reverses its rotational direction.

Returning to FIG. 9B, the operation of the brake controller circuit 224 will now be described. Initially it is noted that comparator 274 normally asserts a high, $\overline{\text{BRAKE-TRIGGER}}$ signal. Consequently a high signal is asserted by NAND gate 360. The high signal produced by NAND gate 360 is applied to the inputs of NOR gates 362 and 364.

The high signal produced by NAND gate 360 inhibits the assertion of clock pulses by NOR gate 362 to counter 366. This high signal also prevents NOR gate 364 from asserting a BRAKE-ENABLE signal. Thus, this arrangement of the brake controller circuit 224 of this invention prevents the brake controller from asserting a BRAKE-ENABLE signal to the motor control chip 272 unless the motor control chip has first generated some signals indicating the motor rotor 203 is in motion and requires the application of a braking force.

When the motor 14 is being driven in an oscillatory rotation, and at other times, the signals present at the input of comparator 274 may cause the comparator to assert the $\overline{\text{BRAKE-TRIGGER}}$ signal. This signal is asserted low to the brake controller circuit 224. After approximately 10 msec, the time it takes capacitor 256 to discharge, NAND gate 358 transitions from low to high. The high signal from NAND gate 358 is then applied to the motor control circuit NOR gates 273 as the HIGH-DRIVE-INHIBIT signal. As a result of the application of the HIGH-DRIVE-INHIBIT signal, the NOR gates 273 are thus locked to a low output signal. Thus, the NOR gates 273 are locked out from asserting control signals to the boost regulator 278 that would cause the boost regulator to assert the signals necessary to tie the motor windings 202 to the positive battery terminal 206. Thus whenever, the $\overline{\text{BRAKE-TRIGGER}}$ signal is asserted for more than a nominal period of time, the brake controller circuit 224 and the motor controller circuit 216 cooperate to prevent the motor windings from being tied to the positive battery terminal 206.

The high signal asserted by NAND gate 358 is then inverted by NAND gate 360. This low signal is applied to separate inputs of NOR gates 362 and 364. Normally, two high signals are not simultaneously-presented to the inputs of NAND gate 370. Consequently, NAND gate 370 normally asserts a high signal. The high signal from NAND gate 370 is applied to the counter 366 as the RESET signal and as second input signal to NOR gate 364. Since NAND gate 370 normally asserts the RESET signal, counter 366 normally likewise outputs low signals. The low-state output signal from counter 366 is applied to both the second input of NOR gate 362 and the third input to NOR gate 364.

Thus, during the majority of the time the $\overline{\text{BRAKE-TRIGGER}}$ signal is asserted, two of the three input signals to NOR gate 364 are low. The remaining signal is the signal from NAND gate 370. Typically this signal is normally a high signal. However, as the rotor 203 turns, both input signals presented to NAND gate 370 are periodically simultaneously high signals. At these times NAND gate 370 asserts a low signal to the NOR gate 364. At these instances, all three inputs to NOR gate 364 are low so as to cause the gate to assert a BRAKE-ENABLE signal to the motor control chip 272. Since the output signal from NAND gate 370 is only periodically low, NOR gate 364 similarly only periodically asserts the BRAKE-ENABLE signal. In this way the brake controller circuit 224 only periodically causes the motor controller circuit 214 to generate signals to causing a braking force to be applied to the motor rotor 203. An advantage of this features of the invention is that it eliminates any jerking of the motor 14 that would be caused if the rotor 203 was rapidly braked.

Moreover, it will further be observed that the on/off duty cycle and the frequency of the motor sensor signal and the MOTOR-PULSE signal applied to the inputs of NAND gate 370 are a function of rotor speed. Specifically, as motor speed increases, the frequency with which both input signals into NAND gate 370 are high increases while the period of each high pulse decreases. Thus, the frequency with which NAND gate 370 asserts a low signal is likewise directly proportional to rotor speed. Consequently, the frequency with which NOR gate 364 asserts the pulsed BRAKE-ENABLE signal is likewise directly related to motor speed. Thus, at higher speeds the BRAKE-ENABLE signal is pulsed on for small individual time periods so as to further reduce the jerking of the motor 14 as it is braked.

When, the use of the drill unit is not longer required, the surgeon will release the pressure of trigger switch 26 and/or trigger switch 28. The brake controller circuit 224 will assert the BRAKE-ENABLE signal in the normal manner as described above. Eventually, the motor rotor 203 will stop rotating.

Normally, after the rotor 203 stops turning, the motor state signals presented to the input of NAND gate 370 result in the gate generating a high signal. However, there is one arcuate range of stopped rotor positions wherein the resultant motor state signals can cause NAND gate 370 to assert a low signal. If this occurs while the BRAKE-TRIGGER signal is still being asserted, NOR gate 364 can inadvertently assert an unneeded, potentially damaging-inducing BRAKE-ENABLE signal. To eliminate the likelihood of this occurring, when the BRAKE-TRIGGER is enabled, the OSCILLATOR signal-based output signal from comparator 368 is applied through NOR gate 362 to the counter 366 as the clock signal. Since, at this time NAND gate 370 is asserting a $\overline{\text{RESET}}$ signal to the counter 366, the counter will count the pulses from the comparator 368. When the count reaches a certain amount, the output from the counter 368 that is applied to NOR gate 364 will transition from low to high. This will cause the NOR gate 364 to negate the BRAKE-ENABLE signal. Thus, the unneeded BRAKE-ENABLE signal is only asserted from a relatively short amount of time.

The high state output signal from counter 366 is also applied to NOR gate 362. Thus, the high output signal from counter 366 also forces the output of NOR gate 362 low so as to effectively disable the application of clock pulses into the counter 366. The disabling of the clock pulses into the counter 366 effectively latches the output from the counter high. The latching of the output signal from counter 366 high ensures that the output signal of NOR gate 364 is, in burns latched in the $\overline{\text{BRAKE-ENABLE}}$ signal state. When the drill unit 10 is again used, the movement of the rotor 203 will cause NAND gate 370 to again assert a RESET signal to counter 366. The assertion of the RESET signal will force the output from counter 366 low so as to unlatch NOR gate 364.

An explanation of how the motor controller circuit 216 and the brake controller circuit 224 cooperate to brake the rotation of the rotor 203 during post run-up deceleration of the motor is now set forth with reference to the timing diagrams of FIGS. 11A–11E. A surgeon may initially actuate one of the trigger switches 26 or 28 to cause the motor 14 to turn at the maximum speed. This is depicted by line segment 390 in the USER-SPEED timing diagram of FIG. 11A. For many drill units, this maximum speed may between 15,000 and 20,000 RPMs. Line segment 392 of FIG. 11B, which represents the MOTOR-SPEED signal, depicts this maximum speed of the motor 14. Once the motor 14 is so actuated, referred to as a motor "run-up," the surgeon will release some of the pressure on the trigger switch 26 or 28 in effort to cause the motor to run at a slower speed. Downwardly diagonally line segment 394 of FIG. 11A represents the reduction in the USER-SPEED signal and horizontal line segment 396 of the same drawing illustrate the signal once the trigger switch has reached a constant position.

One immediate result of the surgeon releasing pressure on the trigger switch 26 or 28, is that the motor control chip 272 will cease tieing the motor windings 202 to the battery 18. The rotor 203, in turn starts to coast to a lower speed. This coasting is depicted by the downwardly curved section 398 of the MOTOR-SPEED signal timing diagram (FIG. 11B). (Curved section 398 shown exaggerated for purposes of illustration.)

FIG. 11C illustrates how the op amp internal to the motor control chip 272 produces the ERROR signal based on the difference between the USER-SPEED signal and the MOTOR-SPEED signal. As soon as the op amp detects that the USER-SPEED drops only a small distance below the actual speed represented by the MOTOR-SPEED, the op amp rapidly slews the ERROR to its lower minimum output voltage, as is represented by the nearly vertical downwardly directed line segment 402 of FIG. 11C. This downward slew of the output from the motor control chip 272 op amp occurs very rapidly, in some preferred versions of the invention, in approximately 1 microsecond. The downward slew of the ERROR signal thus occurs in response to relatively small differences in the USER-SPEED and MOTOR-SPEED signals. In some versions of the invention, the downward slew occurs in response to signals representing a difference in actual motor rotation and user-commanded motor rotation of 100 rpm or less.

The rapid fall of the ERROR results in the rapid transition of the output from comparator 274 from high to low as is represented by FIG. 11D. The low signal from comparator 274 is recognized by the brake control circuit 224 as the assertion of the BRAKE-TRIGGER signal. Not shown in FIG. 11D is the true pulsed profile of the BRAKE-TRIGGER signal as those pulses are filtered out by capacitor 356.

The assertion of the BRAKE-TRIGGER signal causes the brake controller circuit 224 to assert the BRAKE-ENABLE signal as is represented by FIG. 11E. As shown in FIG. 11E, the brake controller circuit 224 pulses the BRAKE-ENABLE signal through the time period the BRAKE-TRIGGER signal is asserted. In many preferred versions of the invention, the BRAKE-ENABLE signal is pulsed on approximately one-sixth to one-half of the time the BRAKE-TRIGGER is asserted. In more preferred versions of the invention, the BRAKE-ENABLE signal is pulsed on approximately one-third of the time the BRAKE-TRIGGER signal is asserted.

The receipt of the BRAKE-ENABLE signal by the motor control chip 272 causes the chip to apply a braking force to the movement of the motor rotor 203. In the depicted version of the invention motor control chip 272 performs this step by asserting LOW-SIDE-CONTROL signals that tie all of the windings 202a, 202b and 202c to ground. As a result of this rapid braking of the motor rotor 203, the motor rapidly decelerates. This deceleration is represented by the diagonally downward line segment 404 of the MOTOR-SPEED timing diagram (FIG. 11B).

As a result of this deceleration, the MOTOR-SPEED signal quickly falls to the level of the USER-SPEED signal. The op amp internal to the motor control chip 272 quickly responds to this change by rapidly pulling the ERROR speed signal upward as is represented by substantially vertical, upwardly directed line segment 406 of FIG. 11C. The rapid rise in the ERROR signal results in the negation of the BRAKE-TRIGGER signal. The negation of the BRAKE-TRIGGER signal results in a like negation of the BRAKE-ENABLE signal.

It should of course be recognized that, as a consequence of the braking of the rotor 203, the motor speed will initially fall a slight amount below the user-commanded speed. This overshoot is represented in FIG. 11B by the small downwardly directed curve 408. This downward transition also causes a momentary rise in the ERROR signal as represented by upwardly directed curve 410 of FIG. 11C.

Should the surgeon again desire to operate the drill unit 10 at full speed, he/she fully depresses the trigger switch 26 or 28. This will result in the USER-SPEED signal first rising and then stabilizing as is represented by upwardly diagonally directed line segment 412 and then horizontal line segment 414 of FIG. 11A. The increase in the USER-SPEED signal will cause a rise in the ERROR signal. However, once the motor speed catches up to the user-commanded speed, the ERROR signal will fall. mhis rise and fall of the ERROR signal is represented by upward line segment 416 and downward line segment 418 of FIG. 11C. However, neither of these signal transitions will cause comparator 274 to assert the BRAKE-TRIGGER signal.

The drill unit 10 forming the cordless, battery operated surgical tool of this invention is provided with a contactless switch assembly for controlling the ON/OFF state and the speed of the drill. There are no mechanical connections needed between the moving magnets 39, 40 and 41 associated with the trigger assembly and the complementary Hall effect sensors 178, 180 and 182 contained in the sealed module housing 150. Consequently, the drill unit can be exposed to harsh, high temperature, high-humidity and high-pressure sterilizing environments, without any concern that the connection between the switch elements will be degraded.

Still another feature of the disclosed invention is that the Hall effect sensors 178–182 are seated in individual cutouts 172 formed in the housing base plate 152. Consequently, the sensors 178–182 are only separated from the associated magnets 39–41 by the relatively narrow thickness of the molybdenum seal 174. This relatively close placement of the sensors 178–182 adjacent the magnets 39–41 enhances the ability of the sensors to generate signals that accurately represent the displacement of the magnets. Moreover, since the molybdenum forming the seal 174 is magnetically permeable, there is little distortion of the magnetic fields formed by the magnets 39–41 as the fields extend into the sealed module housing 150.

The drill unit 10 of this invention is further arranged so that the switches 26 and 28 that control not just the ON/OFF state and speed of the drill motor 14. Switches 26 and 28 further control the direction of motor rotation. Consequently, all the surgeon using the tool has to do in order to control tool direction is to depress the appropriate trigger switch 26 and/or 28. Since both switches extend forward from the handgrip 16, the surgeon need not have to reposition his/her hand in order to control the direction of motor rotation.

When the motor 14 of the drill unit 10 of this invention is driven in an oscillatory rotation, the motor controller circuit 216 is supplied signals that cause it, during the initial reversal of the rotation of the rotor 203, to both brake the rotor motion and that prevent the circuit from applying energization signals that would cause the rotor to be jerked into reverse rotation. Moreover, after the rotor 203 is actuated into reverse rotation, the motor controller circuit 216 further receives signals from the current sensor circuit 214 that serve to prevent the motor controller circuit 216 from excessively over actuating the rotor 203. Collectively, the presentation of these signals to the motor controller circuit 216 ensure that when the drill unit 10 is driven in an oscillatory motion, that the cyclic reversal of rotor rotation will be smooth and not be the cause of excessive tool vibration.

Still another feature of this invention is that the BRAKE-TRIGGER signal is asserted by the comparator 274 in response to the state of the op amp-generated ERROR signal. This feature of the invention causes the BRAKE-TRIGGER signal, and-the resultant BRAKE-ENABLE signal to be quickly asserted as soon as the MOTOR-SPEED and USER-SPEED signals indicate that the motor 14 is operating faster than the user-commanded speed. This feature of the invention likewise ensures that once the motor speed falls to the user-commanded speed, that the BRAKE-ENABLE signal is quickly negated. The ability of the motor control module 22 of this invention to function in this manner makes it possible to use the module to brake the motor not just when the switches 26 and 28 are returned to the off state but also when it is desirable to deceleration the motor after an initial run-up in motor speed.

Moreover, the brake controller 224 of this invention is configured to prevent the false assertion of the BRAKE-ENABLE signal to the motor controller circuit 216. This prevents the motor control circuit 216 from, in turn, tieing the windings 202 to ground when such a connection is neither required or desirable.

It should be recognized that the foregoing description is for the purposes of illustration only. It will be readily understood that alternative constructions of the surgical tool of this invention can be provided. For example, while the surgical tool has been described as being cordless and battery operated, it should be clear that in some versions of the invention the tool may receive its energization current from a cord connected to a power supply external to the motor.

Also, while in the described version of invention the moving magnet switch assembly is described and illustrated as being used in conjunction with a pistol-type, trigger-finger housing and switch, it should be recognized that in other versions of this invention the switch may be used with different types of housings or located at locations on a housing. It should also be recognized that the describe switch can if necessary be used as a single switch if it is only necessary to control motor speed and not motor direction.

It should also be recognized that, while in the preferred embodiment of the invention, two aligned moving magnet switches are used to control both motor speed and motor direction, that this not a requirement for all versions of the invention. It may be desirable in some versions of the invention to employ other switch assemblies, even switch assemblies with moving contact members, to provide the control offered by this invention.

Similarly, it should be understood that the disclosed circuit for controlling the energization of the motor is merely exemplary of one version of this invention. In other versions of this invention it may, for example, not be necessary to provide the disclosed brake controller circuit 224. Moreover, other versions of the invention may have different circuits for applying energization currents to the motor windings 202 and form monitoring current flow through the windings. Furthermore, while the described version of the invention is formed out of a number of different logic gates and counters, it should be recognized that, in alternative versions of the invention, microprocessor control units may perform many of the same, if not all of, the described signal processing and signal generation.

Also, while in the described versions of the invention Hall effect sensors are employed as the motor sensors 220, in some versions of the invention this feature of the disclosed embodiment may be eliminated. It may, for example, be possible to construct this invention wherein back EMF pulses generated by the windings are monitored by the motor control module in order to evaluate rotor 203 movement. Similarly, it should be recognized that other versions of this invention may not required the brushless DC motor 14 incorporated into the described version of the invention. Therefore, it is the object of the appended claims to cover all such modifications and variations as come within the true spirit and scope of the invention.

The embodiments of the invention in which an exclusive property or privilege is claimed are defined as follows:

1. A motor controller for applying energization signals to a motor configured to be rotated in a forward direction and in a reverse direction at variable speeds in response to the application of selected energization signals thereto, said motor control circuit including:

a speed control circuit connected to a user-set speed switch that monitors the state of the speed switch and that generates a USER-SPEED signal representative of a user-set speed for the motor;

a direction control circuit responsive to a user-set direction signal that generates a FORWARD/REVERSE signal, wherein depending on the state of the user-set direction signal, said direction controller generates a FORWARD/$\overline{\text{REVERSE}}$ signal, a $\overline{\text{FORWARD}}$/REVERSE signal or a signal that oscillates between the FORWARD/$\overline{\text{REVERSE}}$ signal and the $\overline{\text{FORWARD}}$/REVERSE signal;

an energization circuit for receiving the FORWARD/REVERSE signal from the direction control circuit and said USER-SPEED signal from said speed control circuit and that is connected to a power source and the motor, wherein said energization circuit is configured to apply energization signals from the power source to the motor to cause said motor to rotate at a specific speed in response to said USER-SPEED signal and in a specific direction in response to the application of a FORWARD/REVERSE signal thereto, wherein, when said FORWARD/REVERSE signal is in a FORWARD/$\overline{\text{REVERSE}}$ state, said motor controller causes said motor to rotate in the forward direction and when said $\overline{\text{FORWARD}}$/REVERSE signal is in a $\overline{\text{FORWARD}}$/REVERSE state, said motor controller causes said motor to rotate in the reverse direction; and a speed override circuit connected to said direction circuit, that receives the user-set direction signals and that is connected to said energization circuit for controlling the application of energization signals by said energization circuit to the motor, wherein, when said FORWARD/REVERSE signal transitions between the FORWARD/$\overline{\text{REVERSE}}$ and the $\overline{\text{FORWARD}}$/REVERSE signal states, said speed override circuit causes said energization circuit for a period of time to apply zero-speed energization signals to the motor equivalent to those applied when a zero-speed USER-SPEED signal is received regardless of the state of the USER-SPEED signal.

2. The motor control circuit of claim 1, wherein:

a braking circuit selectively asserts a BRAKE signal;

said energization circuit receives the BRAKE signal and, in response to receiving the BRAKE signal, applies signals to the motor to cause braking of the motor; and said speed override circuit is connected to said braking circuit for causing said braking circuit to assert the BRAKE signal when the FORWARD/REVERSE signal transitions between the FORWARD/$\overline{\text{REVERSE}}$ and $\overline{\text{FORWARD}}$/REVERSE signal states.

3. The motor controller of claim 2, wherein:

said speed override circuit is configured to receive said USER-SPEED signal and to selectively forward said USER-SPEED signal to said energization circuit wherein, when said FORWARD/REVERSE signal transitions between the FORWARD/$\overline{\text{REVERSE}}$ and $\overline{\text{FORWARD}}$/REVERSE signals states, said speed override circuit pulses said USER-SPEED signal applied to said energization circuit to the zero-speed USER-SPEED signal for the set period of time; and the USER-SPEED signal is applied to said braking circuit and said braking circuit asserts the BRAKE signal based on the state of said USER-SPEED signal.

4. The motor controller of claim 1, wherein, when the motor is driven in oscillatory rotation and each time the FORWARD/REVERSE signal transitions, said speed override circuit causes said energization circuit to apply zero-speed energization signals to the motor for a fixed period of time.

5. The motor controller of claim 1, wherein said speed override circuit is configured to receive said USER-SPEED signal and to selectively forward said USER-SPEED signal to said energization circuit wherein, when said FORWARD/REVERSE signal transitions between the FORWARD/$\overline{\text{REVERSE}}$ and $\overline{\text{FORWARD}}$/REVERSE signals states, said speed override circuit pulses said USER-SPEED signal applied to said energization circuit to the zero-speed USER-SPEED signal for the period of time.

6. The motor controller of claim 1, further including:

a motor monitor connected to the motor for monitoring the speed of the motor and configured to generate a MOTOR-SPEED signal based on the speed of the motor; and wherein said energization circuit receives said MOTOR-SPEED signal and is configured to apply signals to the motor to cause breaking of the motor when said USER-SPEED signal is less than said MOTOR-SPEED signal.

7. The motor controller of claim 6, wherein said motor monitor includes: at least one sensor unit for monitoring the position of the rotor that generates a sensor signal; and a tachometer connected to receive the sensor signal that, based on the sensor signal, generates the MOTOR-SPEED signal.

8. The motor controller of claim 1, wherein said energization circuit is configured to apply zero-speed energization signals to the motor by inhibiting the application of energization signals to said motor.

9. The motor controller of claim 8, wherein said energization controller is further configured to assert signals to the motor to cause braking of the motor and, when acting on the zero-speed USER-SPEED signals, asserts signals to the motor to cause the braking of the motor.

10. The motor controller of claim 1, further including:

a current sensor connected to the motor to monitor the current drawn by the motor, said current sensor being configured to generate a variable CUR+ signal representative of the current drawn by said motor wherein said CUR+ signal is based on a variable volts/amp ratio established by said current sensor in response to a received current sensor control signal and, wherein:

said energization circuit is connected to said current sensor for receiving said CUR+ signal and is further configured to apply energization signals to said motor based on the magnitude of said CUR+ signal; and said speed overide controller is connected to said current sensor for supplying said current sensor control signal thereto and is further configured so that, when the motor is driven in oscillatory rotation and each time said FORWARD/REVERSE signal transitions, to assert said a current sensor control signal to said current sensor to cause said current sensor to momentarily generate said CUR+ signal based on a first volts/amp ratio and to then generate said CUR+ signal based on a second volts/amp ratio that is different from the first volts/amp ratio.

11. The motor controller of claim 10, wherein the first volts/amp ratio established by said current sensor is greater than the second volts/amp ratio established by said current sensor.

12. A motor controller for applying energization signals to a motor, the motor having a magnetized rotor and a plurality of windings that surround the rotor, the windings being configured to be selectively connected to either a power source or ground so as to cause the energization of the windings, said motor controller including:

a motor monitor connected to the motor for generating a MOTOR-SPEED sensor representative of the speed of the rotor;

a speed controller connected to a user-actuated speed switch, said speed controller configured to generate a USER-SPEED signal in response to the actuation of the speed switch that is representative of a user-selected speed for the rotor;

an energization controller connected to the motor for selectively connecting the windings to a power source or ground, to said motor monitor for receiving said MOTOR-SPEED signal, to said speed controller for receiving said USER-SPEED signal, said motor controller being configured to: connect the windings to the power source or ground in response to said MOTOR-SPEED signal and said USER-SPEED signal so as to actuate the rotor; to connect the windings to the power source or ground to cause the deceleration of the rotor in response to a BRAKE-ENABLE signal; and when said MOTOR-SPEED signal and said USER-SPEED signal indicate the rotor is exceeding the user-selected speed by a given amount, to assert a BRAKE-TRIGGER signal; and a brake controller connected to said motor monitor for receiving said MOTOR-SPEED signal and to said energization controller for receiving said BRAKE-TRIGGER signal, said brake controller being configured to assert said BRAKE-ENABLE signal to said energization controller when said BRAKE-TRIGGER signal is asserted and said MOTOR-SPEED signal indicates the rotor is moving and after said MOTOR-SPEED signal indicates the rotor has stopped moving, to negate the assertion of said BRAKE-ENABLE signal regardless of the state of said BRAKE-TRIGGER signal.

13. The motor controller of claim 12, wherein said energization controller is configured to selectively connect the windings of a DC motor to the power source or ground.

14. The motor controller of claim 12, wherein said brake controller is further connected to said energization controller to inhibit said energization controller from energizing the windings so as to cause the movement of the rotor whenever said BRAKE-TRIGGER signal is asserted.

15. The motor controller of claim 12, wherein said brake controller is configured to cyclically assert said BRAKE-ENABLE signal in an on/off/on/off pattern.

16. The motor controller of claim 15, wherein said brake controller is configured to cyclically assert said BRAKE-ENABLE signal in an on/off/on/off pattern at a frequency that is a function of motor speed.

17. The motor controller of claim 12, wherein said motor monitor includes: at least one sensor unit for monitoring the position of the rotor that generates a sensor signal; and a tachometer connected to receive the sensor signal that, based on the sensor signal, generates the MOTOR-SPEED signal.

18. A motor controller for a motor having a magnetized rotor and a plurality of windings that surround the rotor, the windings being configured to be selectively connected to either a power source or ground so as to cause the energization of the windings, said motor controller including:

a motor monitor connected to said motor for generating a MOTOR-SPEED signal representative of the speed of the rotor;

a speed controller connected to a user-actuated speed switch, said speed controller being configured to generate a USER-SPEED signal in response to an actuation of said speed switch that is representative of a user-selected speed for said rotor;

an energization controller connected to the motor for selectively connecting the windings to the power source or ground, to said motor monitor for receiving said MOTOR-SPEED signal, to said speed controller for receiving said USER-SPEED signal, said energization controller being configured to: connect the windings to the power source or said ground in response to said MOTOR-SPEED signal and said USER-SPEED signal so as to actuate the rotor; to connect the windings to the power source or ground to cause the deceleration of said rotor in response to a BRAKE-ENABLE signal; amplify any difference between said USER-SPEED signal and said MOTOR-SPEED signal to produce an ERROR signal; and compare said ERROR signal to a fixed signal and when said comparison indicates that said MOTOR-SPEED signal exceeds said USER-SPEED signal, to assert a BRAKE-TRIGGER signal; and a brake controller connected to said energization controller for receiving said BRAKE-TRIGGER signal, said brake controller being configured to assert said BRAKE-ENABLE signal to said motor controller when said BRAKE-TRIGGER signal is asserted.

19. The motor controller of claim 18, wherein said energization controller is configured to selectively connect the windings of a DC motor to the power source or ground.

20. The motor controller of claim 18, wherein said brake controller is further connected to the motor monitor for receiving said MOTOR-SPEED signal and is further configured to cyclically assert said BRAKE-ENABLE signal to said energization controller when said BRAKE-TRIGGER signal is asserted and said MOTOR-SPEED signal indicates said motor rotor is turning and, after said motor rotor has stopped turning, to negate the assertion of said BRAKE-ENABLE signal regardless of the state of said BRAKE-TRIGGER signal.

21. The motor controller of claim 20, wherein said brake controller is further connected to said energization controller to inhibit said energization controller from energizing the windings to cause the actuation of the rotor whenever said BRAKE-TRIGGER signal is asserted.

22. The motor controller of claim 18, wherein said brake controller is further connected to said energization controller to inhibit said energization controller from energizing the windings to cause the actuation of the rotor whenever said BRAKE-TRIGGER signal is asserted.

23. The motor controller of claim 18, wherein said brake controller circuit delays asserting said BRAKE-ENABLE signal to said energization controller until said BRAKE-TRIGGER signal has been asserted for a select period of time.

24. The motor controller of claim 18, wherein said brake controller is configured to cyclically assert said BRAKE-ENABLE signal in an on/off/on/off pattern.

25. The motor controller of claim 24, wherein said brake controller is configured to cyclically assert said BRAKE-ENABLE signal in an on/off/on/off pattern at a frequency that is a function of motor speed.

26. The motor controller of claim 18, wherein said motor monitor includes: at least one sensor unit for monitoring the position of the rotor that generates a sensor signal; and a tachometer connected to receive the sensor signal that, based on the sensor signal, generates the MOTOR-SPEED signal.

27. A motor control circuit for a motor configured to be rotated in a forward direction and in a reverse direction at variable speeds in response to the application of selected energization signals thereto, said motor control circuit including:
 a current sensor connected to the motor to monitor current drawn by the motor, said current sensor being configured to generate a variable CUR+ signal representative of the current drawn by the motor wherein said CUR+ signal is based on an adjustable volts/amp ratio established by said current sensor based on a current sensor control signal;
 a motor controller connected to the motor for applying energization signals thereto, and to said current sensor for receiving said CUR+ signal, said motor controller being configured to apply energization signals to the motor to cause said motor to rotate at a selected speed in response to the application of a speed signal applied thereto and in response to said CUR+ signal and in a specific direction in response to the application of a FORWARD/REVERSE signal thereto, wherein when said FORWARD/REVERSE signal is in a FORWARD/REVERSE state, said motor controller causes the motor to rotate in the forward direction and when said FORWARD/REVERSE signal is in a FORWARD/REVERSE state, said motor controller causes the motor to rotate in the reverse direction; and
 a direction controller connected to user-set direction switches for receiving said direction commands and being configured to generate said FORWARD/REVERSE signal for forwarding to said motor controller in response to setting of the direction switches and connected to said current sensor for generating said current sensor control signal, wherein when said direction signals indicate said motor is to be driven in oscillatory rotation, said direction controller cyclically transitions said FORWARD/REVERSE signal between the FORWARD/REVERSE signal state and the FORWARD/REVERSE signal state and, with each said state transition of said FORWARD/REVERSE signal, said direction controller asserts said current sensor control signal to cause said current sensor to momentarily base said CUR+ signal on a first volts/amp ratio and to subsequently base said CUR+ signal on a second volts/amp ratio.

28. The motor control circuit of claim 27, wherein after each said state transition of the FORWARD/REVERSE signal, the first volts/amp ratio upon which said current sensor momentarily basis said CUR+ signal is greater than the second volts/amp ratio upon which said current sensor subsequently basis said CUR+ signal.

29. The motor control circuit of claim 27, wherein said motor controller is configured to selectively connect the windings of a DC motor to the power source or ground.

* * * * *

UNITED STATES PATENT AND TRADEMARK OFFICE
CERTIFICATE OF CORRECTION

PATENT NO : 6 013 991
DATED : January 11, 2000
INVENTOR(S) : Chris Philipp

It is certified that error appears in the above-identified patent and that said Letters Patent is hereby corrected as shown below:

Column 28, line 41; change "breaking" to ---braking---.

Column 29, line 3; change "overide controller" to ---override circuit---.

Column 29, lines 7 & 8; change "to assert said a" to ---to assert a said---.

Column 29, line 25; change "MOTOR-SPEED sensor" to ---MOTOR-SPEED signal---.

Column 29, lines 36 & 37; change "motor controller" to ---energization controller---.

Column 32, line 11; change "receiving said direction commands" to ---receiving direction commands---.

Signed and Sealed this

Twelfth Day of December, 2000

Q. TODD DICKINSON

Attest:

Attesting Officer          Director of Patents and Trademarks